(12) United States Patent
Nentwick

(10) Patent No.: US 8,425,455 B2
(45) Date of Patent: Apr. 23, 2013

(54) BRONCHIAL CATHETER AND METHOD OF USE

(75) Inventor: Brian F Nentwick, Greenfield Center, NY (US)

(73) Assignee: AngioDynamics, Inc., Latham, NY (US)

( * ) Notice: Subject to any disclaimer, the term of this patent is extended or adjusted under 35 U.S.C. 154(b) by 65 days.

(21) Appl. No.: 13/074,536

(22) Filed: Mar. 29, 2011

(65) Prior Publication Data
US 2011/0245665 A1 Oct. 6, 2011

Related U.S. Application Data

(60) Provisional application No. 61/318,999, filed on Mar. 30, 2010.

(51) Int. Cl.
*A61M 29/00* (2006.01)
(52) U.S. Cl.
USPC .................................. 604/96.01; 606/194
(58) Field of Classification Search .......... 600/407–430, 600/473–480, 309, 310; 606/194; 604/96.01, 604/93.01, 122, 129, 500, 509, 99.03
See application file for complete search history.

(56) References Cited

U.S. PATENT DOCUMENTS

| | | | |
|---|---|---|---|
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,447,235 A | 5/1984 | Clarke |
| 4,489,535 A | 12/1984 | Veltman |
| 4,512,765 A | 4/1985 | Muto |
| 4,636,199 A | 1/1987 | Victor |
| 4,676,782 A | 6/1987 | Yamamoto et al. |

(Continued)

FOREIGN PATENT DOCUMENTS

| | | |
|---|---|---|
| EP | 0218275 A1 | 4/1987 |
| EP | 0339501 A2 | 4/1989 |

(Continued)

OTHER PUBLICATIONS

NOVATECH SA, "Resector Balloon," http://www.novatech.fr/en/resector-balloonr.html (2010).

(Continued)

*Primary Examiner* — Sanjay Cattungal
(74) *Attorney, Agent, or Firm* — Ryan D. Artis

(57) ABSTRACT

A catheter assembly and method of using the catheter assembly is provided herein. The catheter assembly has a catheter shaft having an elongated body extending about a longitudinal axis, a proximal portion and a distal portion, an outer surface, and at least one lumen extending therethrough the elongated body at least one means for sealing at least a portion of the lumen of the bronchial vessel. At least a portion of the catheter assembly is configured for insertion into at least a portion of a bronchial vessel of a target lung region. The means for sealing is moveable between a collapsed state and an expanded state. At least a portion of the vessel can be sealed by inflating the means for sealing. The catheter assembly can then be used to infuse a dialysate solution into the target lung region.

27 Claims, 17 Drawing Sheets

U.S. PATENT DOCUMENTS

| | | | |
|---|---|---|---|
| 4,687,471 A | 8/1987 | Twardowski et al. | |
| 4,716,896 A | 1/1988 | Ackerman | |
| 4,723,549 A | 2/1988 | Wholey et al. | |
| 4,756,838 A | 7/1988 | Veltman | |
| 4,772,269 A | 9/1988 | Twardowski et al. | |
| 4,798,585 A | 1/1989 | Inoue et al. | |
| 4,813,929 A | 3/1989 | Semrad | |
| 4,819,637 A | 4/1989 | Dormandy, Jr. et al. | |
| 4,836,204 A | 6/1989 | Landymore et al. | |
| 4,840,172 A | 6/1989 | Augustine et al. | |
| 4,863,426 A | 9/1989 | Ferragamo et al. | |
| 4,885,003 A | 12/1989 | Hillstead | |
| 4,886,496 A | 12/1989 | Conoscenti et al. | |
| 4,886,502 A | 12/1989 | Poirier et al. | |
| 4,889,634 A | 12/1989 | El-Rashidy | |
| 4,921,484 A | 5/1990 | Hillstead | |
| 4,981,477 A | 1/1991 | Schon et al. | |
| 4,986,810 A | 1/1991 | Semrad | |
| 4,987,895 A | 1/1991 | Heimlich | |
| 5,053,013 A | 10/1991 | Ensminger et al. | |
| 5,071,558 A | 12/1991 | Itob | |
| 5,141,499 A | 8/1992 | Zappacosta | |
| 5,156,597 A | 10/1992 | Verreet et al. | |
| 5,186,715 A | 2/1993 | Phillips et al. | |
| 5,188,592 A | 2/1993 | Hakki | |
| 5,209,723 A | 5/1993 | Twardowski et al. | |
| 5,215,530 A | 6/1993 | Hogan | |
| 5,224,933 A | 7/1993 | Bromander | |
| 5,242,415 A | 9/1993 | Kantrowitz et al. | |
| 5,279,564 A | 1/1994 | Taylor | |
| 5,290,263 A | 3/1994 | Wigness et al. | |
| 5,308,325 A | 5/1994 | Quinn et al. | |
| 5,308,338 A | 5/1994 | Helfrich | |
| 5,334,167 A | 8/1994 | Cocanower | |
| 5,391,158 A | 2/1995 | Peters | |
| 5,405,320 A | 4/1995 | Twardowski et al. | |
| 5,439,444 A | 8/1995 | Andersen et al. | |
| 5,484,401 A | 1/1996 | Rodriguez et al. | |
| 5,588,424 A | 12/1996 | Insler et al. | |
| 5,599,311 A | 2/1997 | Raulerson | |
| 5,616,126 A | 4/1997 | Malekmehr et al. | |
| 5,690,620 A | 11/1997 | Knott | |
| 5,697,905 A | 12/1997 | d'Ambrosio | |
| 5,700,252 A | 12/1997 | Klingenstein | |
| 5,752,939 A | 5/1998 | Makoto | |
| 5,830,184 A | 11/1998 | Basta | |
| 5,868,708 A | 2/1999 | Hart et al. | |
| 5,904,648 A | 5/1999 | Arndt et al. | |
| 5,954,745 A | 9/1999 | Gertler et al. | |
| 5,984,896 A | 11/1999 | Boyd | |
| 6,004,339 A | 12/1999 | Wijay | |
| 6,074,374 A | 6/2000 | Fulton | |
| 6,110,192 A | 8/2000 | Ravenscroft et al. | |
| 6,132,397 A | 10/2000 | Davis et al. | |
| 6,258,100 B1 | 7/2001 | Alferness et al. | |
| 6,284,140 B1 | 9/2001 | Sommermeyer et al. | |
| 6,328,689 B1 | 12/2001 | Gonzalez et al. | |
| 6,482,221 B1 | 11/2002 | Hebert et al. | |
| 6,491,706 B1 | 12/2002 | Alferness et al. | |
| 6,520,183 B2 | 2/2003 | Amar | |
| 6,537,976 B1 | 3/2003 | Gupta | |
| 6,589,161 B2 | 7/2003 | Corcoran | |
| 6,592,594 B2 | 7/2003 | Rimbaugh et al. | |
| 6,638,253 B2 | 10/2003 | Breznock | |
| 6,666,858 B2 | 12/2003 | Lafontaine | |
| 6,689,096 B1 | 2/2004 | Loubens et al. | |
| 6,694,979 B2 | 2/2004 | Deem et al. | |
| 6,695,861 B1 | 2/2004 | Rosenberg et al. | |
| 6,837,886 B2 | 1/2005 | Collins et al. | |
| 6,847,848 B2 | 1/2005 | Sterzer et al. | |
| 6,860,847 B2 | 3/2005 | Alferness et al. | |
| 6,941,950 B2 | 9/2005 | Wilson et al. | |
| 6,942,681 B2 | 9/2005 | Johnson | |
| 6,960,189 B2 | 11/2005 | Bates et al. | |
| 6,994,689 B1 | 2/2006 | Zadno-Azizi et al. | |
| 7,011,094 B2 | 3/2006 | Rapacki et al. | |
| 7,036,510 B2 | 5/2006 | Zgoda et al. | |
| 7,100,616 B2 | 9/2006 | Springmyer | |
| 7,331,940 B2 | 2/2008 | Sommerich | |
| 7,331,949 B2 | 2/2008 | Marisi | |
| 7,412,977 B2* | 8/2008 | Fields et al. | 128/200.24 |
| 7,434,578 B2 | 10/2008 | Dillard et al. | |
| 7,451,765 B2 | 11/2008 | Adler | |
| 7,476,203 B2 | 1/2009 | DeVore et al. | |
| 7,533,671 B2 | 5/2009 | Gonzalez et al. | |
| 7,544,301 B2 | 6/2009 | Shah et al. | |
| 7,549,984 B2* | 6/2009 | Mathis | 604/509 |
| 7,632,291 B2 | 12/2009 | Stephens et al. | |
| 2002/0049370 A1 | 4/2002 | Laufer et al. | |
| 2002/0112729 A1 | 8/2002 | DeVore et al. | |
| 2002/0147462 A1 | 10/2002 | Mair et al. | |
| 2003/0127090 A1 | 7/2003 | Gifford et al. | |
| 2003/0154988 A1 | 8/2003 | DeVore et al. | |
| 2003/0164168 A1 | 9/2003 | Shaw | |
| 2003/0195385 A1 | 10/2003 | DeVore | |
| 2003/0212412 A1 | 11/2003 | Dillard et al. | |
| 2003/0228344 A1* | 12/2003 | Fields et al. | 424/423 |
| 2004/0055606 A1 | 3/2004 | Hendricksen et al. | |
| 2004/0068228 A1 | 4/2004 | Cunningham | |
| 2004/0200484 A1 | 10/2004 | Springmeyer | |
| 2004/0206349 A1 | 10/2004 | Alferness et al. | |
| 2004/0210248 A1 | 10/2004 | Gordon et al. | |
| 2005/0061322 A1 | 3/2005 | Freitag | |
| 2005/0066974 A1 | 3/2005 | Fields et al. | |
| 2005/0267407 A1 | 12/2005 | Goldman | |
| 2005/0288684 A1* | 12/2005 | Aronson et al. | 606/108 |
| 2005/0288702 A1* | 12/2005 | McGurk et al. | 606/192 |
| 2006/0004400 A1* | 1/2006 | McGurk et al. | 606/192 |
| 2006/0009748 A1* | 1/2006 | Mathis | 604/509 |
| 2006/0020347 A1 | 1/2006 | Barrett et al. | |
| 2006/0079838 A1 | 4/2006 | Walker et al. | |
| 2006/0079845 A1 | 4/2006 | Howard et al. | |
| 2006/0149123 A1 | 7/2006 | Vidlund et al. | |
| 2006/0173490 A1 | 8/2006 | Lafontaine et al. | |
| 2006/0283462 A1* | 12/2006 | Fields et al. | 128/207.14 |
| 2007/0096048 A1 | 5/2007 | Clerc | |
| 2007/0295336 A1 | 12/2007 | Nelson et al. | |
| 2007/0295337 A1 | 12/2007 | Nelson et al. | |
| 2008/0027343 A1* | 1/2008 | Fields et al. | 600/529 |
| 2008/0171985 A1 | 7/2008 | Karakoca | |
| 2008/0190434 A1 | 8/2008 | Wai | |
| 2008/0210243 A1 | 9/2008 | Clayton et al. | |
| 2008/0236593 A1 | 10/2008 | Nelson et al. | |
| 2008/0249503 A1* | 10/2008 | Fields et al. | 604/506 |
| 2008/0283065 A1 | 11/2008 | Chang et al. | |
| 2008/0306427 A1 | 12/2008 | Bailey | |
| 2008/0312599 A1 | 12/2008 | Rosenberg | |
| 2009/0018206 A1 | 1/2009 | Barkan et al. | |
| 2009/0038752 A1 | 2/2009 | Weng et al. | |
| 2009/0081272 A1 | 3/2009 | Clarke et al. | |
| 2009/0114226 A1* | 5/2009 | Deem et al. | 128/205.24 |
| 2009/0138014 A1 | 5/2009 | Bonutti | |
| 2009/0157166 A1 | 6/2009 | Singhal et al. | |
| 2009/0171280 A1 | 7/2009 | Samuel et al. | |
| 2009/0186850 A1 | 7/2009 | Kiribayashi et al. | |
| 2009/0301480 A1* | 12/2009 | Elsakka et al. | 128/202.16 |
| 2009/0306544 A1* | 12/2009 | Ng et al. | 600/581 |
| 2009/0306545 A1* | 12/2009 | Elsakka et al. | 600/581 |
| 2011/0017207 A1* | 1/2011 | Hendricksen et al. | 128/200.24 |
| 2011/0130834 A1* | 6/2011 | Wilson et al. | 623/9 |
| 2011/0152678 A1* | 6/2011 | Aljuri et al. | 600/427 |

FOREIGN PATENT DOCUMENTS

| | | |
|---|---|---|
| EP | 0533511 A1 | 3/1993 |
| EP | 1442765 A1 | 4/2004 |
| EP | 1061983 B1 | 11/2004 |
| EP | 1406685 B1 | 11/2008 |
| EP | 1424970 B1 | 12/2008 |
| WO | 98/10745 | 3/1998 |
| WO | 2004080347 A2 | 9/2004 |
| WO | 2006130194 A2 | 12/2006 |
| WO | 2007123690 A2 | 11/2007 |
| WO | 2009046176 A1 | 4/2009 |
| WO | 2009135070 A1 | 11/2009 |

OTHER PUBLICATIONS

Numata, et al., "Association Between An Increased Surface Area of Peritoneal Microvessels And A High Peritoneal Solute Transport Rate," Peritoneal Dialysis International, vol. 23, pp. 116-122, International Society for Peritoneal Dialysis (2003).
Palmer, "Dialysate Composition in Hemodialysis and Peritoneal Dialysis," Atlas of Diseases of the Kidney vol. 5 chap. 2 at 1-8, Current Medicine, Inc. (1999).
Palmer, "The Dialysis Prescription and Urea Modeling," Atlas of Diseases of the Kidney, vol. 5, chap. 6, pp. 1-8, Current Medicine, Inc. (1999).
Park, et al., "Use of a Fogarty Catheter as a Bronchial Blocker Through a Single-lumen Endotracheal Tube in Patients with Subglottic Stenosis," Anaesthesia and Intensive Care, vol. 31, No. 2, pp. 214-216, International Anesthesiology Research Society (2003).
Popp, et al., "Accuracy of implanted port placement with the use of the electromagnetic CathTrack catheter locator system," Journal of Vascular Access, vol. 6, pp. 9-12 (2005).
Putnam, "The Living Peritoneum as a Dialyzing Membrane," American Journal of Physiology, vol. 63, No. 3, pp. 548-565 (1923).
Ross, et al., "Dialysis Modality Selection in the Elderly Patient with End-stage Renal Disease: Advantages and Disadvantages of Peritoneal Dialysis," Advances in Peritoneal Dialysis, vol. 6., pp. 11-17 (1990).
Royal Prince Alfred Hospital Intensive Care Service, "Intensive Care Service Nursing Policy & Procedures—Intercostal Catheter," (retrieved from http://intensivecare.hsnet.nsw.gov.au/five/doc/icc_uwsd_S_rt_rpa.pdf) (2004).
Saeed, "Bronchial Catheter Guide for Introduction of a Bronchial Catheter," Chest, vol. 38, pp. 162-164, American College of Chest Physicians (1960).
Sam, et al., "Composition and clinical use of hemodialysates," Hemodialysis International, vol. 10, pp. 15-28 (2006).
Scannell, "Rupture of the Bronchus Following Closed Injury to the Chest—Report of a Case Treated by Immediate Thoracotomy and Repair," Annals of Surgery, pp. 127-130 (1951).
Schroder, "Optimal peritoneal dialysis: choice of volume and solution," Nephrol Dial Transplant, vol. 19, pp. 782-784 (2004).
Sheth, et al., "Pleural dialysis in acute renal failure," Clinical Nephrology, vol. 6, No. 2, pp. 370-374 (1976).
Shin, et al., "Bronchial Catheterization with a TIPS Dilator After Failure of Conventional Technique," AJR, vol. 187, pp. W299-W301, American Roentgen Ray Society (2006).
Shrestha, et al., "Inter plueral catheter technique for perioperative pain management," Kathmandu University Medical Journal, vol. 1, No. 1, pp. 46-47 (2003).
Snyder, et al., "Body size and outcomes on peritoneal dialysis in the United States," Kidney International, vol. 64, pp. 1838-1844 (2003).
State of Queensland Australia, "Intercostal Catheter Insertion," (retrieved from http://www.health.qld.gov.au/consent/documents/thoracics_04.pdf) (2008).
Strippoli, et al., "Catheter-Related Interventions to Prevent Peritonitis in Peritoneal Dialysis: A Systematic Review of Randomized, Controlled Trials," Journal of the American Society of Nephrology, vol. 15, pp. 2735-2746 (2004).
Topulos, et al., "Accurate Quantification of Fractional Blood Volume in Lung Tissue," Proceedings of the International Society of Magnetic Resonance Medicine, vol. 10 (2002).
University at Buffalo, "Chest Tube Insertion," http://apps.med.buffalo.edu/procedures/chesttube.asp?p=7 (2010).
Wilkie, "Icodextrin 7.5% Dialysate Solution (Glucose Polymer) in Patients with Ultrafiltration Failure: Extension of CAPD Technique Survival," Peritoneal Dialysis International, vol. 17(1), pp. 84-87 (1997).
Witowski, et al., "Peritoneal Dialysis: A Biological Membrane with a Nonbiological Fluid," Contributions to Nephrology vol. 163 at 27-34 (2009).
Woredekal, "Does Peritoneal Dialysis Have Any Advantages or Disadvantages Over Hemodialysis?" aakpRENALIFE vol. 17 No. 5 (2002) (retrieved from http://www.aakp.org/print-version/dsp_library_art.cfm?art=244, Sep. 14, 2009).
Angiodynamics Inc., "Workhorse II PTA Balloon Catheter," http://www.angiodynamics.com/uploads/pdf/090710-042440_WorkHorse%20II%20Promotional%20Literature.pdf (2010).
Arndt, "Wire-guided Endobronchial Blockade: An Alternative Means For Achieving One-lung Ventilation," The Internet Journal of Anesthesiology, vol. 4, No. 1 (2000).
Baxter International, "Introduction to Peritoneal Dialysis," Module 4 at 1-17 (retrieved from http://nursing.ucsfmedicalcenter.org/education/InService/docs/KidneyFxnPD4.pdf) (2007).
Baxter International, "Possible Problems & Disadvantages of Peritoneal Dialysis," http://www.renalinfo.com/us/treatment/end_stage_kidney_failure/peritoneal_dialysis/possible_problems_with_peritoneal_dialysis.html (2006).
Bekci, et al., "An Adenoid Cystic Carcinoma Case Treated with Resector Balloon," J Bronchol, vol. 15, No. 1, pp. 64-66 (2008).
Blake, "Advantages and Disadvantages of Automated Peritoneal Dialysis Compared to Continuous Ambulatory Peritoneal Dialysis," Peritoneal Dialysis International, vol. 19, supp. 2 (1999).
Bouffard, et al., "Pulmonary Gas Exchange During Hemodialysis," Kidney International, vol. 30, pp. 920-923, International Society for Nephrology (1986).
Brodsky, et al., "Tracheal Diameter Predicts Double-Lumen Tube Size: A Method for Selecting Left Double-Lumen Tubes," Anesthesiology & Analgesia, vol. 82, pp. 861-864, International Anesthesiology Research Society (1996).
Campos, "An Update on Bronchial Blockers During Lung Separation Techniques in Adults," Anesthesia & Analgesia, vol. 97, pp. 1266-1274, International Anesthesiology Research Society (2003).
Caron, et al., "Bronchial Erosion by an Indwelling Central Venous Catheter," Chest, vol. 106, pp. 1917-1918, American College of Chest Physicians (1994).
Chagnac, et al., "Effect of Increased Dialysate Volume on Peritoneal Surface Area among Peritoneal Dialysis Patients," Journal of the American Society of Nephrology, vol. 13, pp. 2554-2559 (2002).
Chagnac, et al., "The Peritoneal Membrane in Peritoneal Dialysis Patients: Estimation of Its Functional Surface Area by Applying Stereologic Methods to Computerized Tomography Scans," Journal of the American Society of Nephrology 10 at 342-46 (1999).
Choi, et al., "Peritoneal Dialysis," Medicine, vol. 31, Iss. 6, pp. 70-73 (2003).
Cook Medical, "Arndt Endobronchial Blocker," http://www.cookmedical.com/cc/dataSheet.do?id=3988 (2009).
Davies, "Mitigating peritoneal membrane characteristics in modern peritoneal dialysis therapy," Kidney International, vol. 70, pp. S76-S83 (2006).
Davies, "Peritoneal Solute Tansport—We Know it is Important, but What is it?," Nephrol Dial Transplant vol. 15, pp. 1120-1123 (2000).
Devuyst, "Molecular mechanisms involved in the peritoneal membrane exposed to peritoneal dialysis," Nefrologia, vol. XXIII., supp. 3, pp. 32-37 (2003).
Devuyst, et al., "Aquaporin-1 in the peritoneal membrane: implications for peritoneal dialysis and endothelial cell function," Biol. Cell, 97(9), pp. 667-673 (2005).
Douglas, et al., "The capacity of the air passages under varying physiological conditions," Journal of Physiology, vol. 145(4), pp. 235-238, The Physiological Society (1912).
Fabbrini, et al., "Peritoneal exposure model in the rat as a tool to unravel bio(in)compatibility of PDF," Nephrol Dial Transplant, vol. 21, supp. 2, pp. ii8-ii11 (2006).
Fischbach, et al., "Measurement by Magnetic Resonance Imaging of the Peritoneal Membrane in Contact with Dialysate in Rats," Advances in Peritoneal Dialysis, vol. 21, pp. 17-20 (2005).
Fischbach, et al., "The Influence of Peritoneal Surface Area on Dialysis Adequacy," Peritoneal Dialysis International 25 supp. 3 at S137-S140, Proceedings of the 1st Joint ISPD/EuroPD Congress (2005).
Flessner, et al., "Increasing Peritoneal Contact Area During Dialysis Improves Mass Transfer," Journal of the American Society of Nephrology, vol. 12, pp. 2139-2145 (2001).
Garland, et al., "Measurement of Extravascular Lung Water in Hemodialysis Patients Using Blood Ultrasound Velocity and Optical Density Dilution," ASAIO Journal, vol. 48, iss. 4, pp. 398-403, American Society of Artificial Internal Organs (2002).
Gjessing, "Pleural Dialysis," Acta Medica Scandinavica, vol. 182, fasc. 2, pp. 259-261 (1967).

Goffen, "Proper Needle Size for Performing Cervical Epidural Injections," Anesthesiology 75(1), pp. 166, International Anesthesiology Research Society (1991).

Gokal, et al., "Peritoneal Catheters and Exit-Site Practices Toward Optimum Peritoneal Access: 1998 Update," Peritoneal Dialysis International, vol. 18, pp. 11-33, International Society for Peritoneal Dialysis (1998).

Gokal, et al., "Peritoneal dialysis," The Lancet, vol. 353, pp. 823-828 (1999).

Groen, et al., "Angiography of the Bronchial Circulation in Bronchial Carcinoma by Means of Subtraction Technique: Its Value in Regional Infusion," Chest, vol. 48, pp. 634-640, American College of Chest Physicians (1965).

Gulli, et al., "Chest Tube Insertion," Gale Encyclopedia of Surgery, The Gale Group Inc. (retrieved from http://www.healthline.com/galecontent/chest-tube-insertion) (2004).

Hannallah, "The Univent Tube: Bronchial Cuff Inflation," Anesthesiology, vol. 75, pp. 165-166, International Anesthesiology Research Society (1991).

Hannallah, et al., "A Comparison of the Reliability of Two Techniques of Left Double-Lumen Tube Bronchial Cuff Inflation in Producing Water-Tight Seal of the Left Mainstem Bronchus," Anesthesia & Analgesia, vol. 87, pp. 1027-1031, International Anesthesiology Research Society (1998).

Herth, et al., "Endoscopic Drainage of Lung Abscesses—Technique and Outcome," Chest, vol. 127, pp. 1378-1381, American College of Chest Physicians (2005).

Karaagac, et al., "Management of Central Airway Obstruction Caused by Submucosal Lesions Using Resector Balloon," J Bronchol vol. 15 No. 2 at 83-86 (2008).

Karakoca, et al., "A New Endoluminal Resection Technique and Device: Resector Balloon," Annals of Thoracic Surgery, vol. 85, pp. 628-631 (2008).

Karasawa, et al., "Rapid Deflation of the Bronchial Cuff of the Double-Lumen Tube After Decreasing the Concentration of Inspired Nitrous Oxide," Anesthesia & Analgesia, vol. 95, pp. 238-242, International Anesthesiology Research Society (2000).

Kiernan, et al., "Comparison of Continuous Ambulatory Peritoneal Dialysis-Related Infections with Different 'Y-Tubing' Exchange Systems," Journal of the American Society of Nephrology, vol. 5, pp. 1835-1838 (1995).

King Edward Memorial I Princess Margaret Hospitals, "Intercostal Catheter Insertion," Neonatology Clinical Guidelines § 2 at 6-9 (retrieved from http://www.kemh.health.wa.gov.au/services/nccu/guidelines/documents/7242.pdf) (2009).

Krediet, et al. "Peritoneal Membrane Failure in Peritoneal Dialysis Patients," Blood Purification, vol. 20, pp. 489-493 (2002).

Kuno, "On the Amount of Blood in the Lungs," Journal of Physiology, vol. 51(3), pp. 154-158 (1917).

Kurihara, et al., "The Ribs: Anatomic and Radiologic Considerations," Radiographics, vol. 19, pp. 105-119 (1999).

Lindholm, "Pleural dialysis in a case of acute renal failure," Acta Medica Scandinavica, vol. 165, fasc. 3, pp. 239-240 (1959).

Locatelli, et al., "Optimal composition of the dialysate, with emphasis on its influence on blood pressure," Nephrol Dial Transplant, vol. 19, No. 4, pp. 785-796 (2004).

Luongo, "Peritoneal Dialysis Fact Sheet," Nephrology Nursing Journal, vol. 30(2), pp. 248-253 (2003).

Macklem, et al., "Bronchial pressures and dimensions in health and obstructive airway disease," J. Appl. Physiol., vol. 18(4), pp. 699-706, American Physiological Society (1963).

Medical Control Board of the Emergency Physicians Foundation, "Tension Pneumothorax Decompression," Prehospital Operational Standards protocol III.25 at III.25.1-III.25.8 (1998).

Mohan, et al., "Fiberoptic-Guided Fogarty Catheter Placement Using the Same Diaphragm of an Adapter Within the Single-Lumen Tube in Children," Anesthesia & Analgesia, vol. 95, pp. 1241-1242, International Anesthesiology Research Society (2002).

Moncada, et al., "Tracheal and Bronchial Cartilaginous Rings: Warfarin Sodium-induced Calcification," Radiology, vol. 184, pp. 437-439 (1992).

Mowbray, et al., "Intercostal catheterisation—An alternative approach to the paravertebral space," Anaesthesia, vol. 42, pp. 958-961, The Association of Anaesthetists of Gt Britain and Ireland (1987).

National Health Service of the United Kingdom, "Dialysis—Advantages and Disadvantages," (retrieved from http://www.nhs.uk/Conditions/Dialysis/Pages/Advantages-and-disadvantages.aspx) (2009).

* cited by examiner

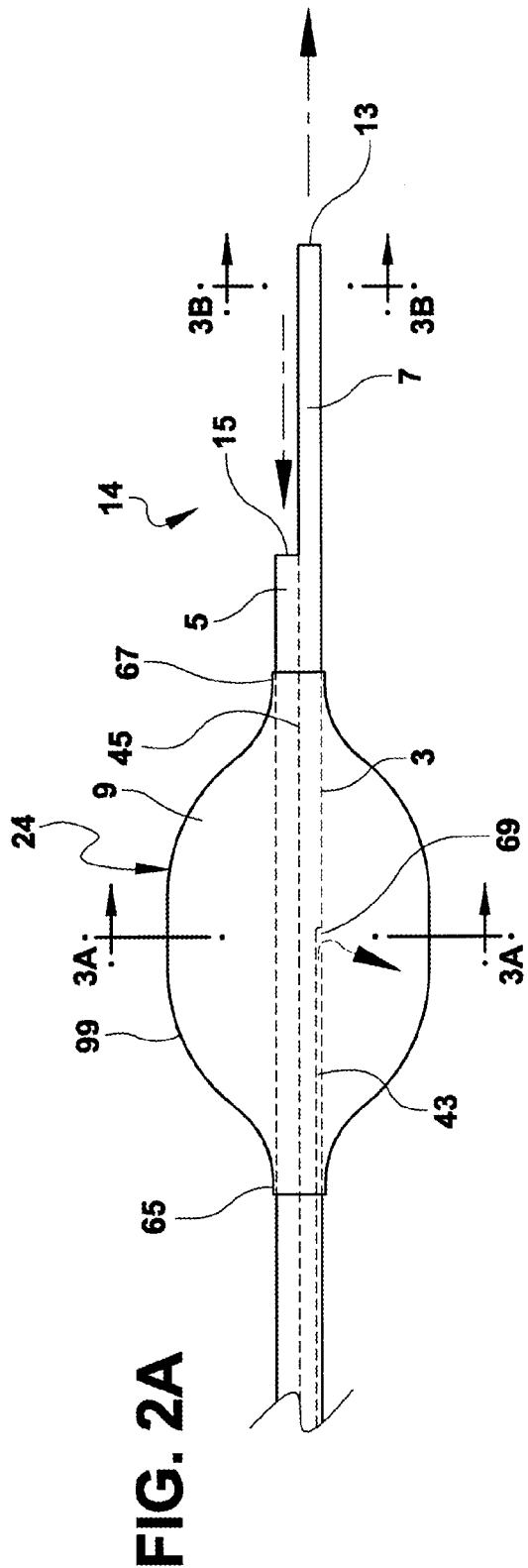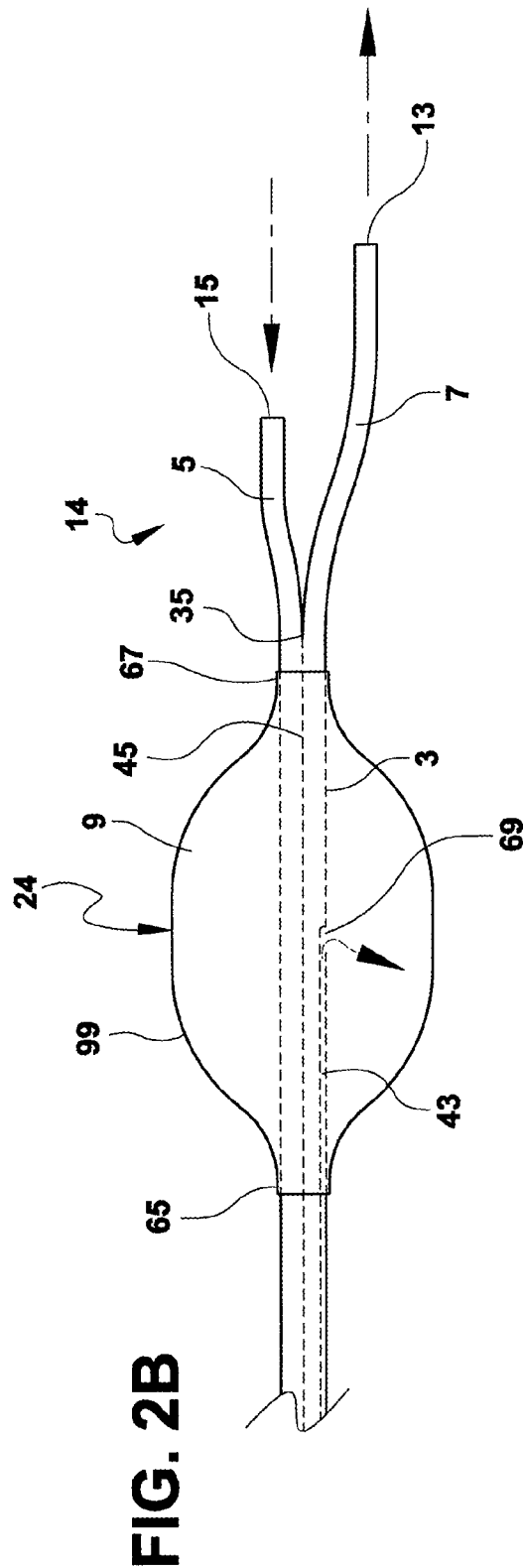

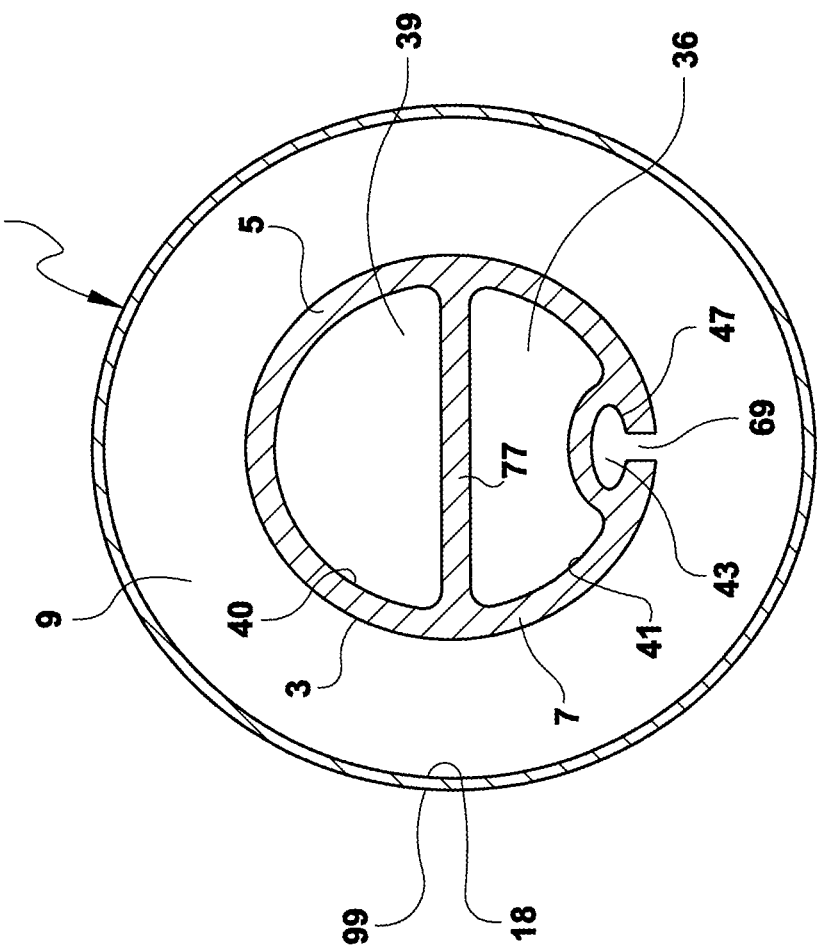
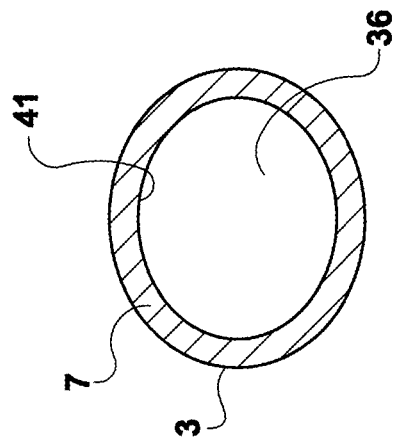
FIG. 3A
FIG. 3B

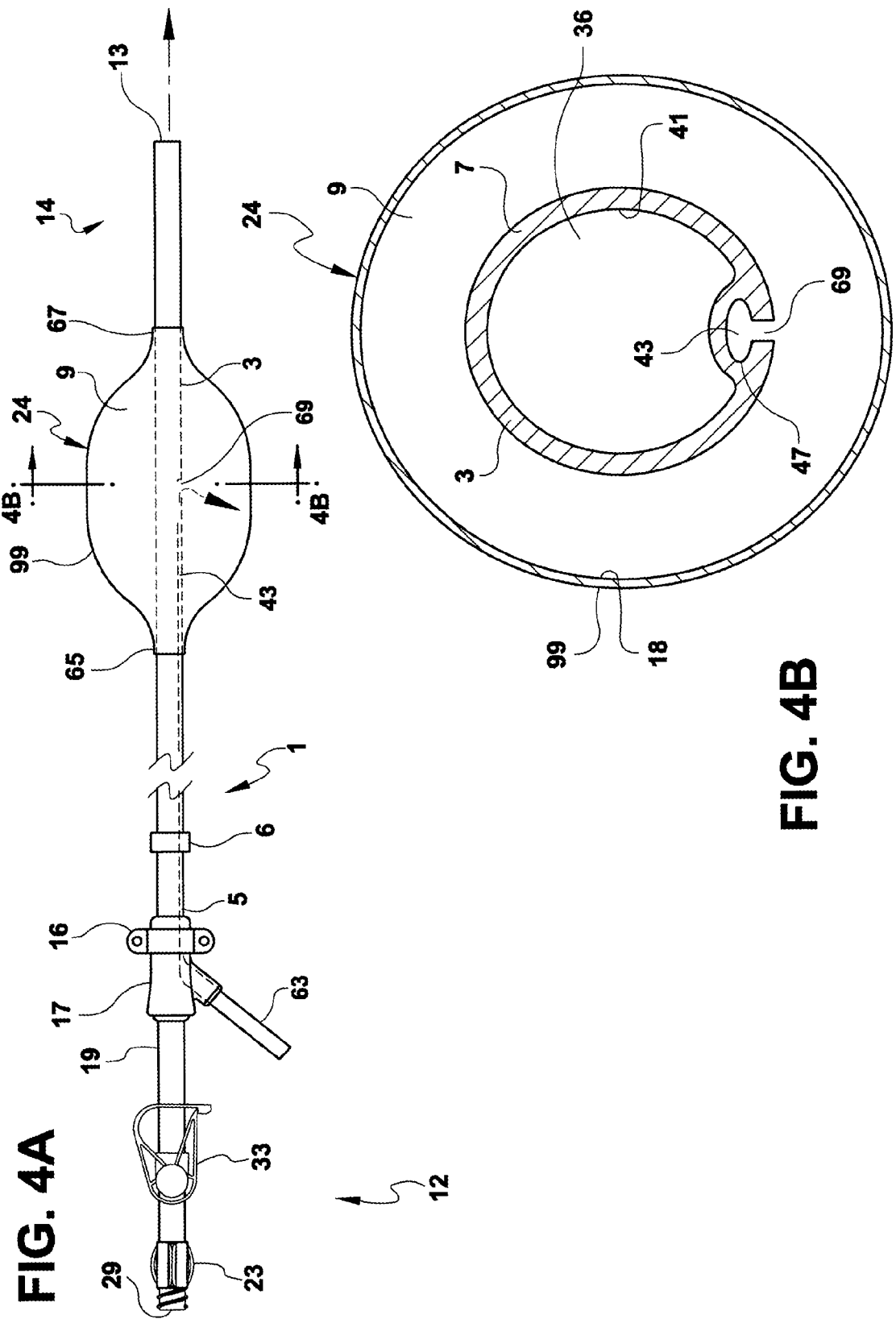

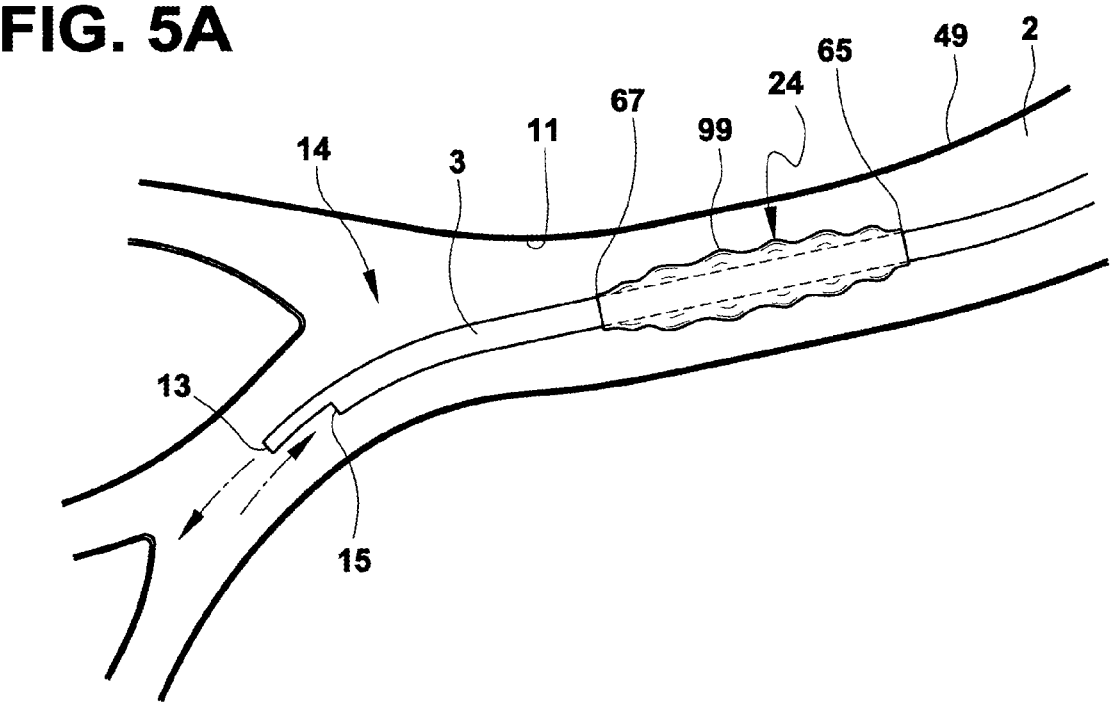
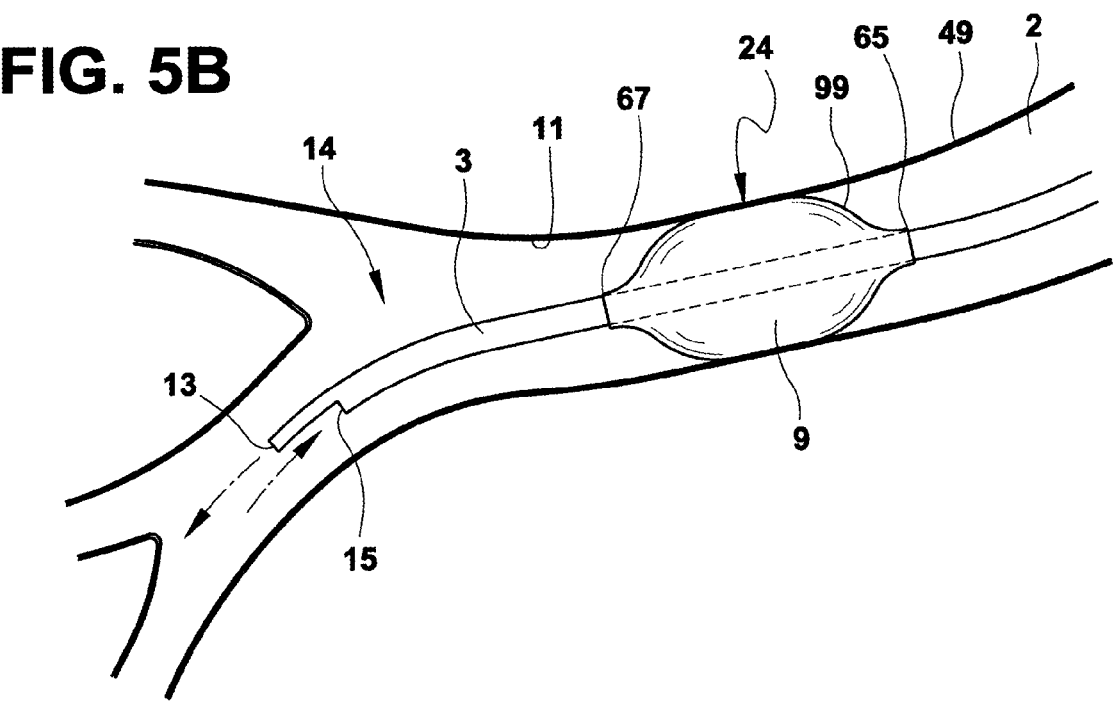

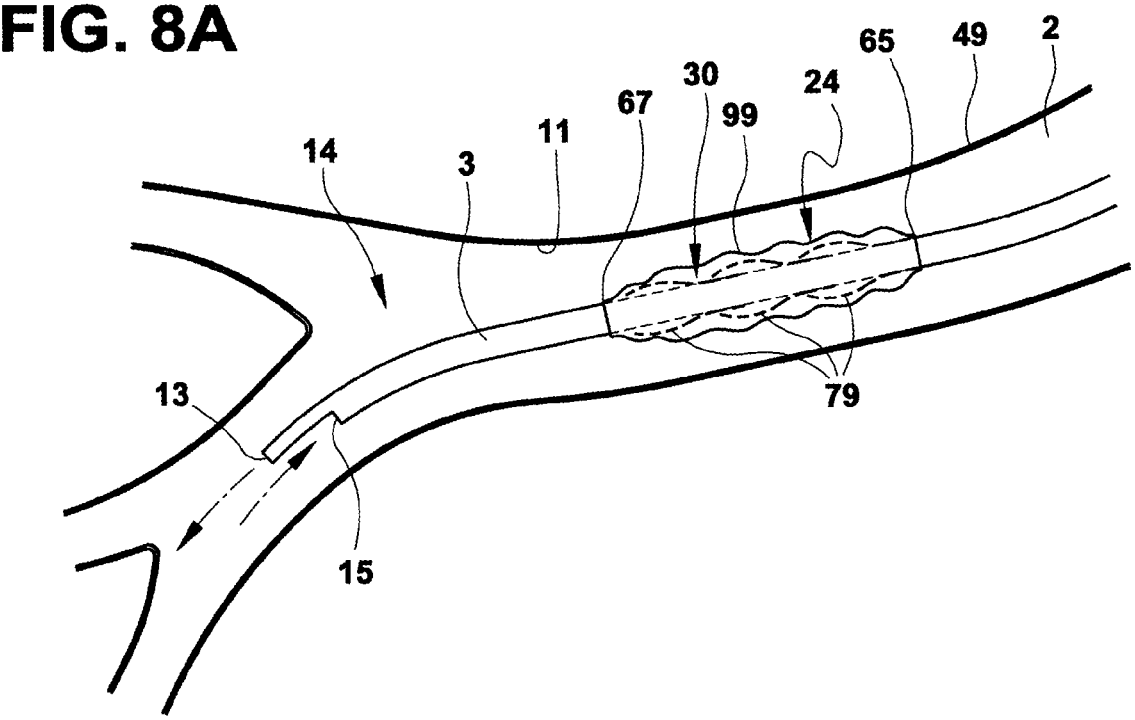
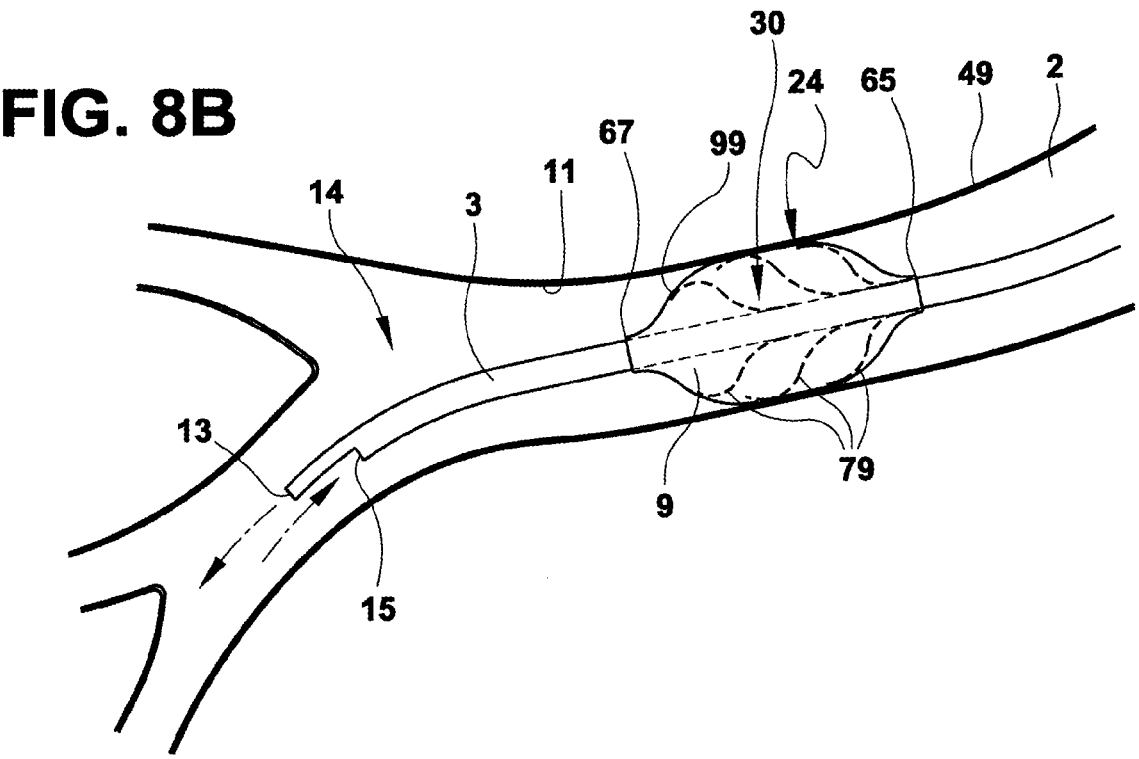

BRONCHIAL CATHETER AND METHOD OF USE

TECHNICAL FIELD

The present invention relates to catheters and more particularly, a dialysis catheter and method of treatment using the dialysis catheter.

BACKGROUND OF THE INVENTION

Peritoneal dialysis (PD) is a form of renal replacement therapy that is used in the management of end stage renal failure (ESRF). PD enables the removal of nitrogenous waste products and water from the body, using peritoneal dialysis fluid (PDF) infused via a catheter into the peritoneal cavity. PD is usually performed by the patient at home and is a continuous therapy, which means that it is designed to work all day, every day.

To perform peritoneal dialysis, a catheter is surgically placed through a patient's abdominal wall. Sterile dialysis solution flows into the peritoneum through the catheter, and solute and fluids are exchanged between the peritoneal capillary blood and the dialysis solution in the peritoneal cavity across the peritoneal membrane, the semi-permeable lining of the abdomen, which acts as a filter. The physiological basis of dialysis across the peritoneum involves diffusion, convective transport, and osmosis. Solutes diffuse between the blood and dialysate by diffusive and convective transport, according to their concentration gradient. The rate of solute transport can be variable in different patients, depending on the membrane permeability and the functional surface area of the peritoneal membrane that is in contact with the dialysate. Used dialysis solution remains in the peritoneal cavity for a desired period of time as waste products diffuse from the blood across the peritoneum and into the dialysate. When the dialysate reaches chemical equilibrium, excess fluid is removed by the process of osmosis, using a hypertonic glucose solution, and the fluid is drained from the peritoneal cavity and replaced with new solution. The time when the solution is in the peritoneal cavity and dialysis is occurring is called the dwell time. Most adults use 2 to 3 liters of solution for each dwell. However, the amount of solution and the duration of the dwells are adjusted to each patient's individual needs and can change over time. After the dwell is completed, the solution is drained from the body and replaced with fresh solution in an exchange procedure, and wastes and excess fluid move from the blood vessels in the peritoneal membrane into the solution by diffusion.

Advantages of peritoneal dialysis include the use of relatively simple equipment, treatments that can be maintained by an ambulatory patient, and an overall improvement in patient health due to the frequency of treatments. Disadvantages of peritoneal dialysis include logistical challenges associated with transporting an external catheter or other machines and large volumes of dialysate fluid. PD typically needs to be performed every day, thereby disrupting a patient's daily schedule. PD can also increase the risk of a patient's peritoneum becoming infected with bacteria (peritonitis). Peritonitis, or an inflammation of the peritoneum, can damage the peritoneal membrane, resulting in permeability changes and temporary or permanent catheter withdrawal. The dialysis fluid that is typically used in peritoneal dialysis can cause a reduction in protein levels, low rates of removal of molecular-weight nitrogenous waste products, ultrafiltration, or inadequate fluid removal and extravascular volume expansion, loss of protein, amino acids, and other nutrients into the dialysate, which can all lead to a lack of energy, and in some cases, malnutrition. Some people using peritoneal dialysis also experience a rise in their blood cholesterol levels, which can put them at a greater risk of developing a cardiovascular disease, such as heart attack, or stroke. Other disadvantages can include weight gain, constipation, exit site infections, tunnel infections, stretching of the abdomen, backaches or shoulder pains, fluid leaking, hernias, hemorrhoids, constipation, loss of appetite from glucose absorption, protein and amino acid losses, and fatigue from continuous use, and the like, especially in elderly patients.

The surface area of the peritoneum and diffusion gradients in the large volume of dialysate used during dialysis (approximately 2 to 3 liters of solution) can adversely impact dialysis adequacy. The peritoneal surface area is composed of three exchange entities: the anatomic area, the contact area, and the vascular area. The amount of perfused capillaries within the peritoneal membrane determines the effective peritoneal surface area (EPSA), i.e., the functional area of exchange between the blood and the dialysate. It has been shown that only a fraction of the peritoneum is exposed to dialysate fluid during dialysis. The EPSA that is exposed to dialysate fluid during dialysis prevents some patients from having an effective peritoneal membrane surface area that is suitable for peritoneal dialysis.

There exists a need in the art for an improved dialysis catheter and method of dialysis using a dialysis catheter that will allow for increased filtration during dialysis using a different bodily organ that has a higher effective surface area, such as the lungs, compared to the peritoneum, thereby providing an alternative to peritoneal dialysis. A vascular access catheter and method has not yet been proposed that would solve this problem, thereby avoiding many of the negative side effects of peritoneal dialysis described above.

A dialysis catheter is described herein that provides a long term solution for patients undergoing peritoneal dialysis.

A dialysis catheter is provided that can be inserted into a highly vascularized organ with a large surface area, such as, for example, the lung, as an alternative to using the peritoneum during peritoneal dialysis.

It is a purpose of the invention described herein to provide a dialysis catheter that can be inserted into the bronchi of the lungs as an alternative to the peritoneum.

It is a purpose of the invention described herein to provide a dialysis catheter that can provide an alternative form of infusion and drainage of fluid during dialysis.

It is a purpose of the invention described herein to provide a catheter that can be equipped with at least one sealing means to isolate a target lung region, thereby allowing the isolated area to be filled with dialysate fluid in a manner similar to peritoneal dialysis.

It is a further purpose of this invention to provide a method of using the catheter described herein to perform dialysis treatment within a portion of a patient's lung.

Various other objectives and advantages of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention can be found in the Detailed Description of the Invention.

SUMMARY

A catheter is provided herein that has a catheter shaft having an elongated body extending about a longitudinal axis, a proximal portion and a distal portion, an outer surface, and at least one lumen extending therethrough the elongated body. At least a portion of the distal portion of the catheter assembly is configured for insertion into at least a portion of a bronchial vessel. The catheter assembly also has at least one means for sealing at least a portion of the lumen of the bronchial vessel. The means for sealing has a proximal end, a distal end, an inner surface, and an outer surface. At least a portion of the inner surface is operatively coupled to at least a portion of the outer surface of the catheter shaft. The means for sealing is moveable between a collapsed insertion state and an expanded sealing state, and the means for sealing is in fluid communication with the at least one lumen.

A method of using a catheter is provided herein that involves providing an indwelling catheter assembly that has a catheter shaft having an elongated body extending about a longitudinal axis, a proximal portion and a distal portion, an outer surface, at least one lumen extending therethrough the elongated body; and at least one means for sealing at least a portion of a vessel of a patient. The means for sealing is operatively connected to at least a portion of the outer surface of the catheter shaft. The method further involves inserting the distal portion of the catheter into a target lung region; sealing at least a portion of the catheter by inflating or expanding the means for sealing within the target lung region; and infusing a fluid into the target lung region.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 2A illustrates an enlarged sectional view of the distal portion of the catheter shaft of FIG. 1.

FIG. 2B illustrates an enlarged sectional view of an alternative embodiment of the distal portion of the catheter shaft of FIG. 1.

FIG. 3A illustrates an enlarged cross-sectional view of the distal portion of the catheter of FIG. 1 along line 3A-3A.

FIG. 3B illustrates a cross-sectional view of the distal portion of the catheter of FIG. 1 along line 3B-3B.

FIG. 4A illustrates a plan view of an alternative embodiment of the catheter of FIG. 1.

FIG. 4B illustrates an enlarged cross-sectional view of the catheter of FIG. 4A along line 4B-4B.

FIG. 5A illustrates a perspective view of the distal portion of the catheter of FIG. 1 in a deflated state positioned within a portion of a patient's bronchial vessel.

FIG. 5B illustrates a perspective view of the distal portion of the catheter of FIG. 1 in an inflated state inserted into a portion of a patient's bronchial vessel.

FIG. 8A illustrates a perspective view of another embodiment of the distal portion of the catheter of FIG. 1 in a deflated state positioned within a portion of a patient's bronchial vessel.

FIG. 8B illustrates a perspective view of the distal portion of the catheter of FIG. 1 in an inflated state positioned within a portion of a patient's bronchial vessel.

DETAILED DESCRIPTION OF THE INVENTION

Figure 1:
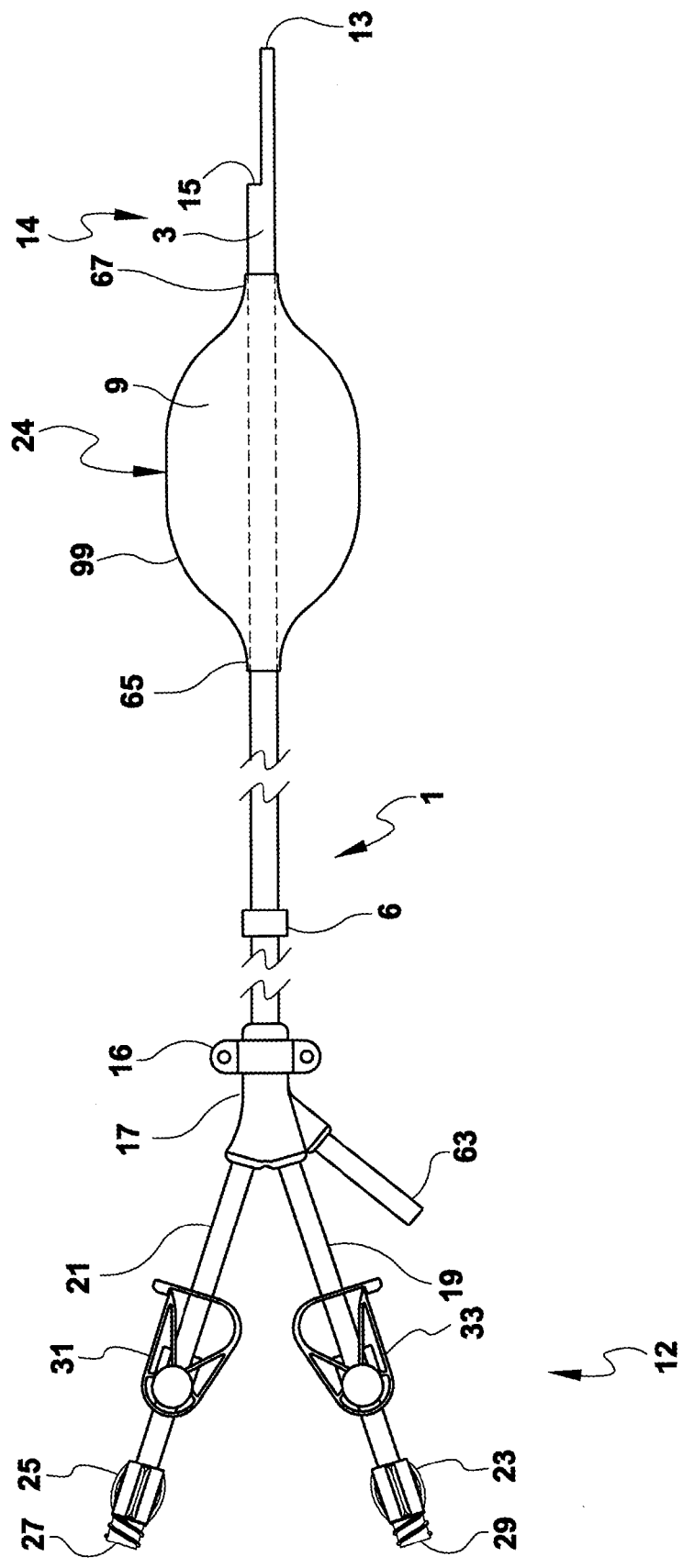
FIG. 1 illustrates a plan view of one embodiment of the dialysis catheter presented herein.

The present invention can be understood more readily by reference to the following detailed description and the examples included therein and to the Figures and their previous and following description. The drawings, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Ranges can be expressed herein as from "about" to one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, the words "proximal" and "distal" refer to directions away from and closer to, respectively, the insertion tip of the catheter in the catheter assembly. The terminology includes the words above specifically mentioned, derivatives thereof, and words of similar import.

Other than in the operating examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components and/or materials be a member comprising at least these recited components and/or materials, and can further include other non-recited components and/or materials.

Examples provided herein, including those following "such as" and "e.g.," are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

"Polymer" or "polymeric" refers to a natural, recombinant, synthetic, or semisynthetic molecule having in at least one main chain, branch, or ring structure having two or more repeating monomer units. Polymers broadly include dimers, trimers, tetramers, oligomers, higher molecular weight polymers, adducts, homopolymers, random copolymers, pseudocopolymers, statistical copolymers, alternating copolymers, periodic copolymers, bipolymers, terpolymers, quaterpolymers, other forms of copolymers, substituted derivatives thereof, and mixtures thereof, and narrowly refer to molecules having one or more repeating monomer units. Polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric, can be ionic or non-ionic, can be neutral, positively charged, negatively charged, or zwitterionic, and can be used singly or in combination of two or more thereof.

As used herein, "substantially", "generally", and other words of degree are relative modifiers intended to indicate permissible variation from the characteristic so modified. It is not intended to be limited to the absolute value or characteristic which it modifies, but rather possessing more of the physical or functional characteristic than its opposite, and preferably, approaching or approximating such a physical or functional characteristic. "Optional" or "optionally" means that the subsequently described element, event or circumstance can or cannot occur, and that the description includes instances where said element, event or circumstance occurs and instances where it does not.

Referring now in detail to the drawings, in which like reference numerals indicate like parts or elements throughout the several views, in various embodiments, presented herein is an exemplary catheter, such as a dialysis catheter, and a method of treatment using the dialysis catheter in a human lung.

FIGS. 1 through 3B illustrate one exemplary embodiment of a multilumen vascular access catheter, such as a dialysis catheter. The catheter assembly 1 has a proximal end 12 and a distal end 14. At least a portion of the proximal end 12 of the catheter assembly 1 can be configured to be positioned outside of a human body. At least a portion of the distal end 14 of the catheter assembly 1 can be configured to be inserted into at least a portion of an anatomical bodily opening of a human body, such as, but not limited to, a target location in a human lung. In one aspect, the target location in a human lung can comprise a bronchial vessel. Bronchial vessel is defined herein to mean a bronchus or a bronchi of a human lung, including a transplanted lung or artificial lung. Thus, the terms "bronchial vessel" and "bronchi" are used herein interchangeably.

In one aspect, the catheter assembly 1 can comprise an elongate cylindrical flexible unitary body or catheter shaft 3 that has a proximal end, a distal end, and extends about a longitudinal axis that is positioned within a single plane, and at least one lumen. In one exemplary embodiment, the catheter shaft 3 can be about 9 Fr to about 19 Fr, or about 3 mm to about 6.33 mm in outer diameter and about 2 mm to about 5 mm in inner diameter. Although the dimensions of the catheter shaft 3 can vary, based on patient anatomy, the outer diameter of the catheter shaft 3 can be smaller than the inner diameter of a human bronchial vessel, such that at least a portion of the catheter shaft 3 is configured to be inserted into at least a portion of the lumen of a bronchial vessel. In one exemplary aspect, the catheter shaft 3 can have a uniform diameter. Alternatively, although not illustrated, in one aspect, the catheter shaft 3 can have a wider diameter at the proximal end of the shaft 3 and a narrower diameter at the distal end of the shaft 3 to compensate for changes in anatomy during insertion. The catheter shaft 3 can have a length of about 30 cm to about 78 cm. More particularly, the catheter shaft 3 can have a length of from about 30 cm to about 60 cm. In one exemplary aspect, the catheter shaft 3 can have a length of about 50 cm.

At least a portion of the catheter shaft 3 can be flexible, yet semi-rigid, and biasable and can be configured to conform to or align with the shape of an anatomical bodily opening, such as, but not limited to, a trachea, bronchus, bronchi, or any other desired bodily cavity in order to navigate the tortuous pathway between a trachea and a target location of a human lung. The distal portion 14 of the catheter shaft 3 can be configured to be more flexible compared to the proximal portion 12 of the catheter shaft 3 to allow the distal portion 14 of the catheter to be more easily navigated into to a lumen of a bronchial vessel. At least a portion of the catheter shaft 3 can be pre-curved (not shown) or it can be straight, as illustrated. The distal portion 14 of the catheter shaft 3 can have a pre-curved, biased, or asymmetric shape with respect to the longitudinal axis of the catheter shaft 3. This pre-curved or asymmetric shape can facilitate better steering of the distal portion 14 past the carina 20 of the lungs, described herein, where the catheter can frequently get stuck. A curved tip catheter is advantageous because it can be easy to selectively insert the tip into the bronchus. This pre-curved shape can also help the distal portion 14 be better aligned with and positioned within a bronchial vessel.

In one aspect, the elongate catheter shaft 3 of the catheter assembly 1 can be comprised of any suitable biocompatible plastic or elastomeric material, such as, but not limited to, polyurethane and polyethylene, or soft silicone elastomers. In one exemplary aspect, the catheter shaft 3 can be composed of a Carbothane® material. At least a portion of the outer surface of the catheter shaft 3 can be coated with one or more of the following: coagulation enhancing agents to stop bleeding, mucolytic agents to reduce or eliminate mucus production, anti-inflammatory agents, anti-proliferative agents, analgesics, antibiotic coatings, antimicrobial coatings, antifungal coatings, hydrophilic coatings, other lubricious coatings, regenerative agents for parenchymal regeneration, or any combination thereof.

Although not illustrated, the catheter shaft 3 can have a plurality of side ports defined therein at least a portion of an outer surface of the catheter shaft 3 at the distal end 14 of the catheter shaft 3 to allow for additional fluid flow. In one aspect, at least a portion of the catheter shaft 3 can have at least one radiopaque indicia that can be incorporated anywhere along at least a portion of the catheter shaft 3. The radiopaque indicia can be placed along the catheter shaft 3 to aid a practitioner in indicating the depth of insertion of the catheter shaft 3 into a target location within a human lung. The radiopaque indicia can provide information pertaining to the position or the orientation of the catheter or detection within the body by any suitable imaging technique. In one aspect, the radiopaque material can include, but is not limited to, barium sulfate, bismuth subcarbonate, zirconium dioxide, cadmium, tungsten, gold, tantalum, bismuth, platinum, iridium, and rhodium.

A bifurcate or hub 17 surrounds at least a portion of the outer surface of the proximal portion 12 of the catheter shaft 3. The catheter assembly 1 can have at least a first extension tube 19 and a second extension tube 21 and at least a first extension tube clamp 33 and a second extension tube clamp 31. The clamps 33, 31 can be releasably attached to at least a portion of each extension tube 19, 21 for selectively opening and closing the tubes 5, 7 (FIG. 2A). In one aspect, optionally at least one of the catheter extension tubes 19, 21 can have at least one pre-curved portion (not shown). The at least one pre-curved portion can enable the extension legs to extend downward against a patient's body once the distal portion of the catheter assembly 1 has been placed into at least a portion of an anatomical bodily opening of a patient. This design can be beneficial because it can provide greater comfort for the patient. The hub 17 also has an inflation port 63 having a proximal end and a distal end that can be used for injection of fluids or air into at least one of the catheter lumens.

The catheter assembly 1 described herein has at least a first catheter hub connector or luer connector 23 and a second catheter hub connector or luer connector 25 for joining to an infusion pump or other injection or aspiration device in order to provide intravascular access to the patient. In one aspect, the distal end 14 of the catheter terminates in two distal tips or apertures 13, 15. The distal tips 13, 15 of the catheter assembly 1 can be atraumatic. The tips 13, 15 can be made of a soft material, such as silicone, urethane, and the like, that facilitates movement of the tips 13, 15. In one aspect, the tips 13, 15 can be rounded, tapered, or cone-shaped instead of blunt or square to facilitate steering of the catheter through the trachea and bronchial vessels. Although not illustrated, in one aspect, the catheter shaft 3 can comprise at least one additional aperture that can be defined in the side wall of the catheter shaft 3. More particularly, the catheter shaft 3 can comprise a plurality of apertures defined in the side wall of the catheter such that the apertures are in fluid communication between at least one lumen of the catheter shaft 3 and the exterior of the catheter shaft 3. The apertures can be positioned within the catheter side wall at the distal portion 14 of the shaft 3.

Cuff 6, which facilitates anchoring for tunneled catheters, can optionally be attached to at least a portion of the outer surface of the unitary catheter shaft 3. Cuff 6 can be useful for allowing subcutaneous tissue to grow into the cuff 6 and to help secure the catheter once it is implanted in a patient's body. Cuff 6 can be composed of polyester or Dacron® polyester. The catheter assembly 1 can also have a suture wing 16, which can circumferentially surround the outer surface of the catheter shaft 3.

Referring to FIGS. 2A and 2B, shaft 3 can be comprised of at least one tube. More particularly, the catheter shaft 3 can be comprised of at least a first tube 5 and a second tube 7, each having at least one lumen that extends substantially about the entire length or longitudinal axis of the shaft 3. The tubes 5, 7 can be joined together for at least a portion of their length along an interface 45. The catheter shaft 3 described herein can have a staggered or stepped tip distal tip configuration (FIG. 2A) or a split tip distal tip catheter configuration (FIG. 2B), as well as other types of non-split tip distal tip catheter configurations.

In one aspect, as illustrated in FIGS. 3A and 3B, in one aspect, tubes 5, 7 can comprise at least one lumen. More particularly, tubes 5 and 7 can comprise an aspiration lumen 39 and an infusion lumen 36, respectively. Lumen 39 can be configured to withdraw fluid through lumen 39 under negative pressure. Lumen 36 can be configured to infuse or return fluid to a patient under positive pressure, as described herein. At least one of the lumens 36, 39 can extend substantially longitudinally and independently parallel about the length or longitudinal axis of the shaft 3 from a proximal end 12 to a distal end 14 of the catheter shaft 3. At least one of the lumens can extend substantially along the entire length of the catheter shaft 3. In one aspect, lumen 36 can be positioned on one side of the longitudinal axis, and lumen 39 can be positioned on a second side of the longitudinal axis. In one exemplary embodiment, catheter lumen 36 can be longer than catheter lumen 39, or, alternatively, lumen 39 can be longer than lumen 36. In the embodiment illustrated, the first catheter lumen can be configured to extend deeper into an anatomical bodily opening, such as a bronchial vessel, compared to the second catheter lumen. Lumens 39, 36, are in fluid communication with first and second extension tubes 19, 21, and distal tips 15, 13, respectively. This enables the infusion or aspiration of fluids to and from the lung of a patient. Either of these lumens 36, 39 can be capable of selectively receiving a guide wire, which can be used during insertion of the catheter to a location in a bronchial vessel. Each lumen may be of various sizes and shapes. In another exemplary aspect, the catheter shaft 3 can have a plurality of lumens, such as, but not limited to, two, three or more lumens, if desired.

As illustrated in FIG. 3A, aspiration tube 5 of the catheter shaft 3 can have an inner surface 40, and infusion tube 7 can have an inner surface 41. Arterial tube 5 has inner lumen surface 40 and an outer surface, which is also the outer surface of the catheter shaft 3. In one aspect, venous tube 7 has a venous lumen 36 with an inner lumen surface 41. In one aspect the portion of the catheter tube 5 that is defined between the outer surface of the catheter shaft 3 and the inner lumen surface 40 defines the tube 5 sidewall. The portion of the catheter tube 7 that is defined between the outer surface of the catheter shaft 3 and the inner lumen surface 41 defines the tube 7 sidewall. Each catheter tube can have a substantially equal wall thickness. Alternatively, each catheter tube 5, 7 can have a variable wall thickness. The catheter shaft 3 can have a unitary septum 77, illustrated in FIG. 3A. In one aspect, each catheter lumen of the dual lumen configuration can have a variable shape, such as, but not limited to, D-shaped, oval (FIG. 3B), circular, elliptical, or any other suitable lumen configuration, diameter, material, thickness, or length, in any combination thereof.

The catheter tubes 5, 7 are preferably designed to maximize the cross-sectional diameter of the lumens 36, 39 to achieve increased flow rates during aspiration and infusion. In one aspect, the cross-sectional area of the D-shaped lumens 36, 39 can be substantially equal. Alternatively, one of ordinary skill in the art will recognize that lumens 36, 39 can have different cross-sectional areas. For example, lumen 36 can have a first cross-sectional area, and lumen 39 can have a second cross-sectional area. In one aspect, lumen 36 can have a larger cross-sectional area than lumen 39 along at least a portion of its longitudinal length. Alternatively, in another aspect, lumen 39 can have a larger cross sectional area than lumen 36 along at least a portion of its longitudinal length.

In yet another aspect, as illustrated in FIGS. 4A and 4B, the catheter assembly can be identical to the catheter assembly as described above, except that the catheter only has one lumen and one extension tube. In this configuration, infusion of fluid into the catheter can be established from the proximal end 12 to the distal end 14 and into a patient's lung, and outflow or aspiration from the patient's lung can be selectively established from the distal end 14 of the catheter to the proximal end 12. The single central lumen 36 terminates at the proximal end 12 of the catheter and is fluidly joined to a single extension tube 19, where the catheter can be connected to an infusion pump. Fluid infusion can be carried out under positive pressure, and fluid aspiration can be carried out under negative pressure. "Positive" pressure means that the static pressure in the lumen 36 near the distal end 14 can exceed the static pressure external to the distal end 14. "Negative" pressure refers to conditions where the static pressure external to the distal end 14 exceeds the static pressure in the lumen 36 near the distal end 14.

As illustrated in FIGS. 1 through 4B, at least a portion of the outer surface of the catheter shaft 3 can be surrounded by at least one means for substantially sealing an anatomical bodily opening, such as, but not limited to, a bronchial vessel. The means for sealing the bronchial vessel can be, but is not limited to, an inflatable or expandable member, such as a balloon 24 or similar structure. Although a balloon 24 is described herein as being used as a sealing means, one of ordinary skill in the art will recognize that other means for sealing can be used. The balloon 24 can be movable between a collapsed insertion state and an expanded sealing state.

As illustrated in FIG. 3A, the balloon 24 can have an outer surface 99 and an inner surface 18. The balloon 24 can be disposed at least partially coaxially in surrounding relation around at least a portion of the outer surface of the catheter shaft 3 such that an annular balloon interior cavity 9 is defined between the inner wall 18 of the balloon and the outer surface of the catheter shaft 3. At least a portion of the catheter shaft 3 extends through the cavity 9 of the balloon 24 and carries the balloon 24. The balloon 24 can have a cylindrical section with a maximum diameter that tapers down to reduced diameters at the proximal end 65 and the distal end 67. At least a portion of the inner surface 18 of the proximal end 65 and the inner surface 18 of the distal end 67 of the balloon 24 can be operably connected to at least a portion of the outer surface of the distal portion 14 of the catheter shaft 3 by bonding, welding, clamping, fusing, or any suitable method known in the art. The distal end 67 of the balloon 24 terminates proximally of both of the distal apertures 13, 15. When the proximal end 65 and the distal end 67 of the balloon 24 are secured to the outer surface of the catheter shaft 3, an air tight seal is formed. The distal end 67 of the balloon 24 can terminate between about 2 cm and about 4 cm proximally from the distal end of the most proximal edge of the catheter tips 13, 15.

In one aspect, the balloon 24 can extend longitudinally along the outer surface of the catheter shaft and can be between about 10 mm and about 40 mm in length. In yet another aspect, the inner diameter of the proximal and distal ends of the balloon 24 that surround the outer surface of the catheter shaft 3 can be between about 2 mm and about 10 mm in diameter, to form a snug fit around the outer surface of the catheter shaft 3. The maximum inflated diameter of the balloon 24 can be between about 3 mm and about 22 mm in diameter, depending on the size of the patient or the lung cavity treated. More particularly, the maximum diameter of the balloon 24 can be between about 14 mm and about 22 mm. More particularly, the outer diameter of the balloon 24 can be between about 3 mm and about 12 mm. More particularly, the balloon 24 can have a maximum expanded diameter of between about 12 mm and about 16 mm. The maximum diameter of the balloon 24 in the expanded state can be substantially equal to or greater than the inner diameter of a bronchial vessel, such as a bronchi, in order to help form an interference fit between the outer surface 99 of the balloon 24 and the inner wall 11 of the bronchial vessel 49. More particularly, the outer diameter of the balloon 24 can have a diameter, when inflated, that is between about 0.5 mm to about 1.00 mm more than the outer diameter of the balloon 24. One of ordinary skill will recognize that the diameter of the balloon 24 can be varied in response to the amount of pressurized air that is infused into the cavity 9 of the balloon 24.

In one aspect, the wall thickness of the balloon 24 can be optimized to ensure a substantially complete seal between the inner wall of the bronchial vessel and the outer wall of the balloon. At least a portion of the balloon 24 can be configured to conform to the geometry of at least one of the lumen of the trachea and the bronchial vessel where the catheter is placed. In one exemplary embodiment, at least a portion of the outer surface of the balloon 24 can be configured to conform to the lumen of at least one of the trachea and the bronchial vessels to substantially seal the lumen. More particularly, the outer surface 99 of the balloon 24 can be configured to substantially conform to the shape of at least one space between cartilaginous rings located in at least one of: the trachea and the bronchi, thereby forming a substantially complete seal between the outer surface 99 of the balloon 24 and the inner wall 11 of the bronchial vessel. As described herein, the walls of the trachea and the bronchi include C-shaped cartilage rings separated by softer intervening tissue such as fibrous tissue, muscular fibers, mucous membrane, and glands. The tracheal cartilaginous rings vary from fifteen to twenty in number and may be spaced about 1-4 mm apart along the tracheal wall. The rings help stiffen the tracheal wall and help keep the tracheal airway open.

In one aspect, the balloon 24 can be a high strength, high volume, low pressure, balloon with a thin, highly flexible relatively inelastic wall that is readily inflatable under pressure and readily collapsible under vacuum, such that the balloon can stretch a relatively small amount under pressures of up to about 15 atmospheres or more. In one non-limiting example, balloon 24 can have an average burst pressure of between about 2 atmospheres and about 6 atmosphere, and more particularly, between about 4 atmospheres and 6 atmospheres. The balloon can be between about 0.0005 inches and 0.020 inches in thickness.

In one exemplary aspect, the balloon 24 can be made of a lightweight, flexible material, such as, but not limited to, one or more layers of any suitable expandable or distensible material such as nitrile, butyl rubber, viton, nylon, neoprene butanes, thermoplastic polymers, aliphatic polyurethanes, aromatic polyurethanes, thermoplastic polyurethane elastomers, low-density polyethylene, polyethylene terephthalate, polyethylene terephthalate glycol, silicone, natural rubber, synthetic rubber, latex, or any other suitable biocompatible elastomers, or any combination thereof. In one aspect, the balloon 24 can also be made of a combination of materials with a combination of distensibilities, such as, but not limited to those described in U.S. Pat. No. 6,004,339, incorporated herein by reference. The balloon 24 can be distensible and inflatable or deflatable in response to air, fluid, or gases that pass through lumen 43. Fluid is defined herein to mean either fluids or gases, including bodily fluids. In one aspect, the balloon 24 can have at least one radiopaque marker placed on at least a portion of the balloon 24 that can aid in visualization of the balloon during insertion and use. In one aspect, the outer surface 99 of the balloon 24 can be coated with a water soluble lubricant. One of ordinary skill in the art will recognize that the balloon 24 can be any type of suitable balloon known in the art that is configured to be inflated during use. In one exemplary aspect, although only one balloon 24 is illustrated, in one aspect, a plurality of balloons 24 can be positioned therein at the distal end 14 of the catheter shaft 3.

As illustrated in FIGS. 2A through 4B, in one aspect, the interior cavity 9 of the annular balloon 24 can be fluidly connected with at least one lumen of the catheter shaft 3. More particularly, the balloon 24 can be in fluid communication with inflation lumen 43. The inflation lumen 43 has a proximal end and a distal end that can be connected to an inflation source. The proximal end of the inflation lumen 43 can be configured to be operatively and fluidly connected to the distal end of inflation port 63 that is positioned at the proximal end of the catheter. Inflation lumen 43 has an inner wall 47 (FIG. 3A). The inflation lumen 43 is configured to receive fluids, gas, or air. One of ordinary skill will recognize that the inflation lumen 43 can be positioned at other various locations along the catheter shaft 3, provided that the opening 69, described below, is positioned within the balloon 24. Alternatively, although not illustrated, the inflation lumen 43 can be positioned within the wall of the catheter shaft 3 or outside of and adjacent to the outer wall of the catheter shaft 3. At least a portion of the inflation lumen 43 is can be in fluid or gaseous communication with the interior cavity 9 of the balloon 24. If the inflation lumen 43 is positioned within the wall of the catheter shaft 3, this can enable the cross-sectional lumen configuration of lumen 36 to remain substantially equal to lumen 39, thereby maintaining the cross-sectional area of the catheter shaft. Lumen 43 extends from the distal end of the inflation port 63 along a portion of the longitudinal axis of the shaft 3 substantially parallel with infusion and aspiration lumens 36, 39 to at least one opening 69. Opening 69 is defined in the outer surface of the catheter shaft 3 and is positioned proximally of the distal end 67 of the balloon 24 and distally of the proximal end 65 of the balloon 24 and distally of the distal tips 13, 15 of the catheter shaft 3. This enables at least a portion of the inflation lumen 43 to be in fluid communication with at least a portion of the interior cavity 9 of the balloon 24 through opening 69.

The proximal end of the inflation port 63 can be operably connected to and in fluid communication with a means for inflating (not shown) the balloon 24. In one aspect, the means for inflating the balloon 24 can be, but is not limited to, a vacuum, a lockable syringe, a plunger, an infusion source, or the like. In one aspect, the means for inflating can be used to inflate the balloon 24. Any suitable inflation medium can be used to inflate the balloon 24, such as, but not limited to, liquid, air, saline, or any other gas that is suitable for use in patients. When an inflation medium is infused into the balloon 24, the balloon expands radially outwardly. The dimensions of the inflation port 63 and the inflation lumen 43 can be configured to permit the flow of fluids, gases, or air from the inflation port 63 through the inflation lumen 43 and the opening 69 into or from the interior cavity 9 of the balloon 24 during inflation and deflation of the balloon 24. In one aspect, the inflation lumen 43 and the opening 69 can have a diameter of between about 0.2 mm and about 0.4 mm and a length from the proximal end of the hub to opening 69 of between about 5 mm and about 10 mm.

Although not illustrated, in one aspect, the catheter assembly 1 can optionally include a separate means for measuring or indicating the air pressure level or a change in air pressure within the balloon cavity 9 at the distal end of the catheter. The means for measuring air pressure can be, but is not limited to, a balloon, a pressure gauge, or a sensor. The means for measuring the air pressure can be attached to the inflation lumen 43 at the proximal end of the catheter assembly 1 to assist the user in detecting the pressure that is in the balloon 24.

Referring to FIGS. 5A and 5B, in one exemplary aspect, the balloon 24 can be pre-formed in a substantially deflated state before use, between uses, or during passage of the balloon 24 through lumen 2 of a bronchial vessel 49, as illustrated in FIG. 5A. To deflate the balloon 24, a vacuum can be used to remove air from the balloon cavity 9. In the deflated state the balloon 24 can be configured such that at least a portion of the inner surface 16 of the balloon 24 can lie close against the outer surface of the catheter shaft 3. In its collapsed or deflated state, the balloon 24 can have a length of about 10 mm and a minimum transverse dimension or diameter of about 2 mm for insertion and passage through the bronchial vessels. In its deflated state, the balloon 24 can have a diameter that is substantially the same as the outside diameter of the catheter shaft 3. The collapsed diameter of the balloon 24 can be smaller than the inner diameter of the bronchial vessel 49, such that the overall diameter of the catheter is suitable for insertion and passage through a lumen 2 of a bronchial vessel 49 without protruding and interfering with such insertion or engaging the inner wall 11 of the bronchial vessel 49. In all of the embodiments described herein where the balloon 24 is compressed before insertion, the balloon 24 has a first diameter in the expanded or anchoring state and a second diameter in the deflated state. The first diameter is larger than the second diameter.

Alternatively, the balloon 24 can have a pre-formed expanded outer state that is substantially fixed before the distal portion of the catheter assembly is inserted into a bronchial vessel of a target lung region. In its original pre-formed expanded configuration, the balloon 24 can have an expanded state or configuration with a first expanded diameter, as described below. During insertion, the balloon 24 can be deflated and can have a second deflated diameter that is smaller than the first diameter. The balloon 24 can then be allowed to return to its first expanded diameter once the sealing means or balloon 24 is positioned within the bronchial vessel of the target lung region. The pre-formed expanded configuration of the balloon 24 ensures that when the balloon 24 returns to its original form after collapse within the bronchial vessel of the target lung region, the pre-formed balloon 24 will assume a fully expanded state having an outer configuration that can fully expand within the lumen of a bronchial vessel of a target lung region.

After the balloon is inserted into the bronchial vessel, it can be inflated using inflation lumen 43. When inflated, the balloon 24 can have a circular or spherical outer circumference when viewed along a cross-section (FIGS. 3A, 4B). While balloon 24 is generally described herein as having a round, expanded cross-section with a generally uniform single transverse dimension, in other exemplary aspects, the balloon 24 can have an overall oval or elliptical outer shape. The balloon 24 can have any shape having a transverse dimension that can be expanded to contact opposing portions of interior wall 11 of bronchi 49. In one exemplary aspect, when inflated, the balloon 24 can have a maximum diameter of between about 14 mm and about 22 mm. The maximum outer diameter of the expanded balloon can be substantially equal to or greater than the inner diameter of the lumen of bronchial vessel 49. The outer surface 99 of the balloon 24 can provide a smooth and gentle surface during inflation of the catheter assembly 1, such that any trauma to the inner wall 11 of the anatomical bodily vessel is minimized.

In the expanded state the outer surface 99 of the balloon 24 can exert a sufficient outward radial force on the inner surface 11 of the bronchi 49 to maintain the balloon's position within a patient's bronchial vessel, to engage the inner wall 11, and to help prevent migration of the balloon 24 and the catheter. The balloon 24 has a sufficiently dimensioned outer surface area 99 that can provide maximum optimal contact with the inner bronchial wall 11 of the bronchial vessel 49 after it is inserted into the bronchial vessel, while minimizing potential trauma to the bronchial vessel 49. When inflated, the balloon 24 can expand and contract in size to fit within and seal bronchial lumens 2 of various sizes, described herein. The seal prevents fluid from flowing between the interior wall 11 of the bronchi 49 and the outer surface 99 of the balloon 24. The balloon 24 also functions as an anchor and holds the distal portion of the catheter in place within a bronchial vessel 49, thereby minimizing or eliminating any movement of the catheter assembly 1 while in use. The balloon 24 can be deflated before it is removed from the patient's bronchial vessel 49.

Figure 6A:
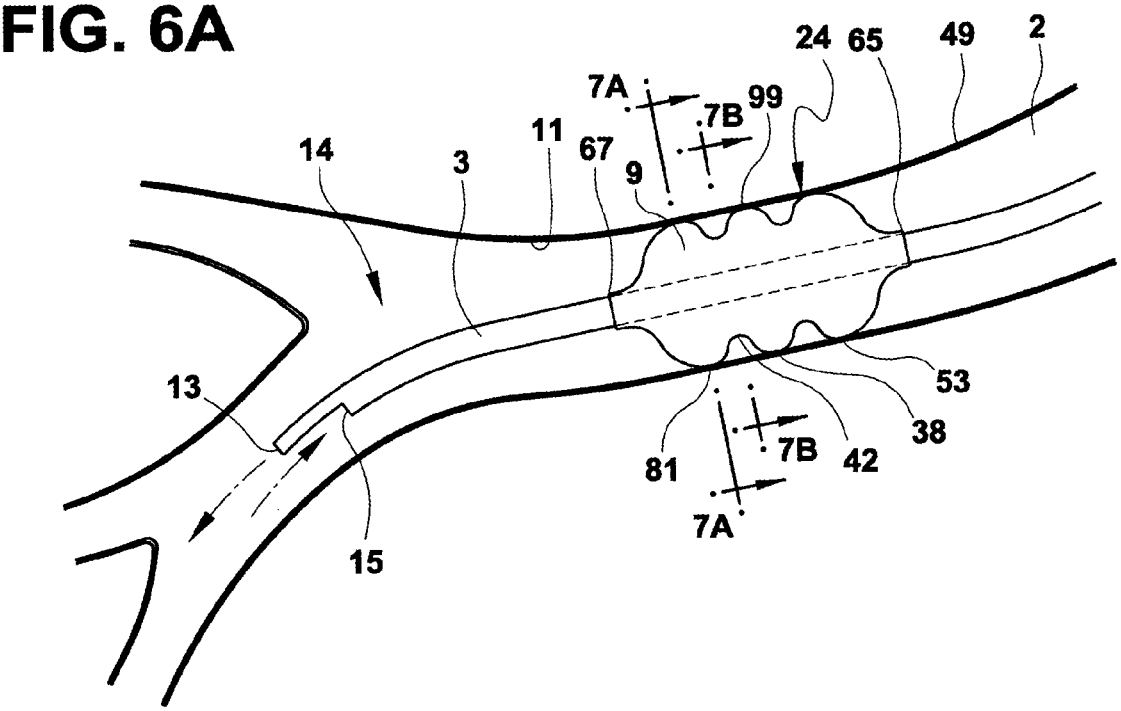
FIG. 6A illustrates a perspective view of another embodiment of the catheter of FIG. 1 positioned within a portion of a patient's bronchial vessel.
Figure 6B:
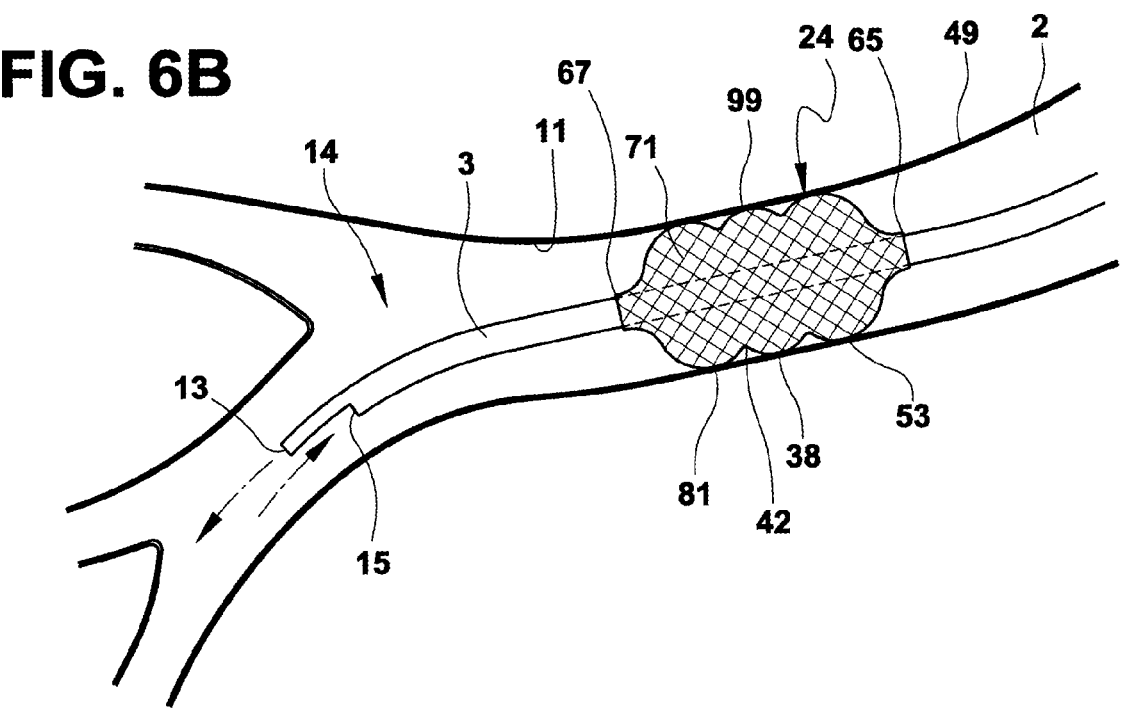
FIG. 6B illustrates a perspective view of another embodiment of the catheter of FIG. 1 positioned within a portion of a patient's bronchial vessel.

Referring to FIGS. 6A and 6B, a second and third embodiment of the sealing means 24 is depicted. In one aspect, the balloon 24 can comprise a plurality of elevated radially extending circumferential ridges 81, 38, 53, each separated by a trough 42. The ridges and troughs form an integral part of the balloon 24 and define a uniform outer surface 99 and a variable diameter of the balloon 24. When the balloon 24 is in the expanded or inflated position, the balloon 24 can be positioned within the lumen 2 of the bronchi 49 such that at least a portion of the outer surface 99 of the balloon along a first ridge 81, a second ridge 38, and a third ridge 53 contact inner wall 11 of the bronchi 49. The outer surface 99 along each ridge can circumferentially contact the inner wall 11 of the bronchi 49 such that the outer circumference of each of the sealing ridges 81, 38, 53 forms a substantially complete seal with the inner wall 11 of the bronchi 49. In another aspect, the ridges and troughs of the balloon 24 can be configured to allow each ridge to align with the intervening tissue spaces between each successive cartilaginous ring. Each successive ridge can be spaced apart between about 1-4 mm to facilitate this alignment. This spacing may allow each ridge to conform more closely to the shape of the tracheal lumen 26 or the inner wall 11 of the bronchial lumen 2, resulting in an improved seal. Alternatively, the ridges may be irregularly spaced apart along the axis of the catheter shaft 3.

Figure 7A:
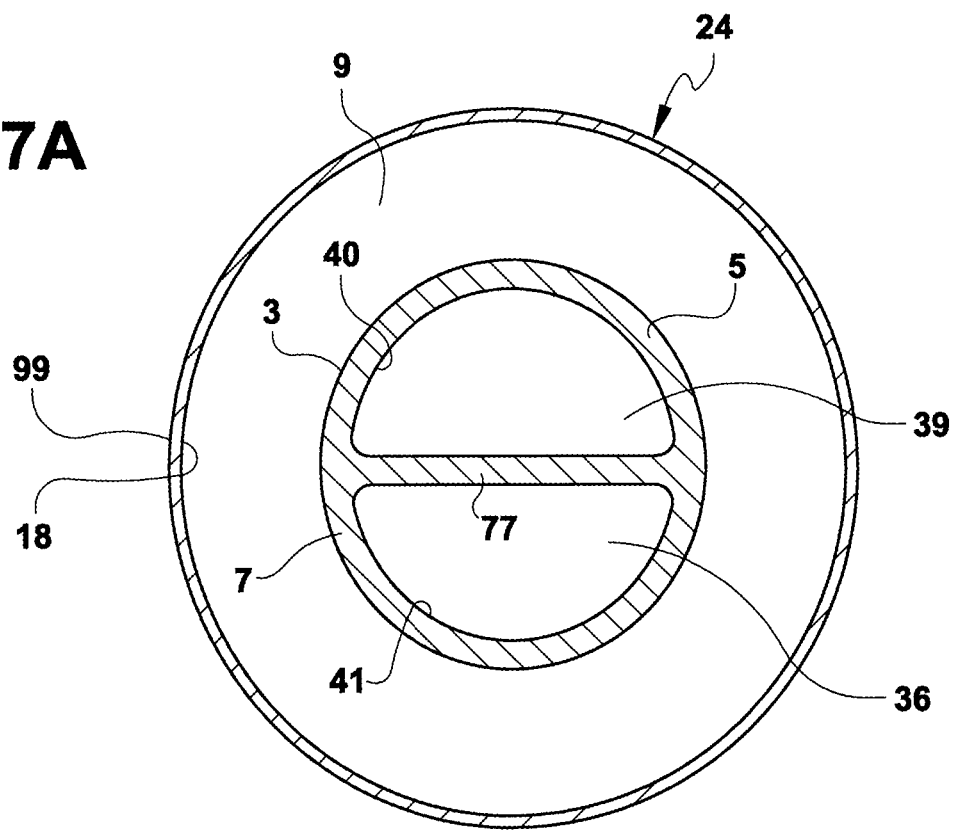
FIG. 7A illustrates an enlarged cross-sectional view of the catheter of FIG. 6A along line 7A-7A.
Figure 7B:
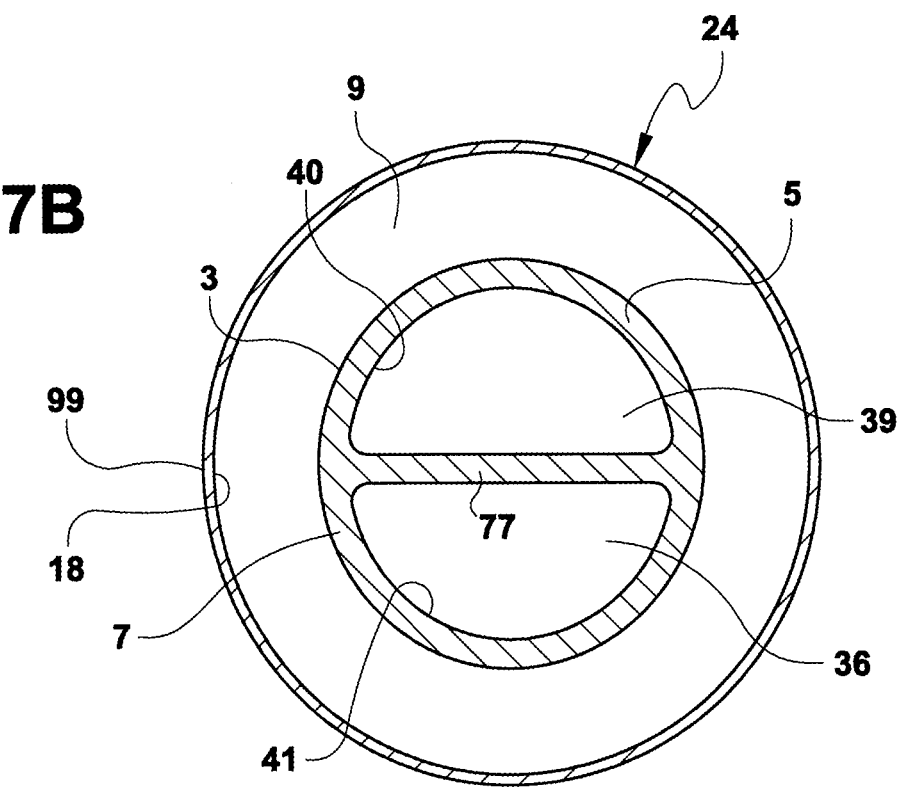
FIG. 7B illustrates an enlarged cross-sectional view of the catheter of FIG. 6A along line 7B-7B.

When viewed from a cross-sectional perspective, as illustrated in FIGS. 7A and 7B, each trough 42 has a lower height and smaller outer diameter compared to the height and outer diameter of each of the sealing ridges 81, 38, and 53. The trough 42 region of the balloon 24 can form a minimal contact or no contact region with the inner wall 11 of the bronchial vessel. In this minimal contact region, the outer surface 99 of the balloon 24 is generally not in contact with the inner wall 11 of the bronchi 49. The smaller the diameter of the trough 42, the larger the gap between the outer surface 99 of the balloon 24 and the inner wall 11 of the bronchi 49. In one aspect, the maximum diameter of each ridge can be substantially equal. The sealing ridges 38, 53, and 81 can be any suitable height, width, shape or dimension, provided that the outer surface of the balloon 24 along at least one ridge forms a substantially complete seal with the inner wall 11 of the bronchial vessel 49. In the embodiments described herein, the balloon 24 has a rounded or circular cross sectional configuration. Together, the series of ridges and troughs can form a curved, undulating, or sinusoidal series of shapes, as viewed from the side (FIGS. 6A and 6B). The outer surface 99 of each ridge can be rounded and smooth, squared, pointed, or any other suitable shape, provided that the shape does not cause trauma to the inner wall 11 of the bronchial vessel 49.

First ridge 81 is capable of withstanding a first pressure that can be exerted at any point of contact between at least a portion of the outer wall 99 of sealing ridge 81 and a portion of the inner wall 11 of the bronchial lumen 2 of the balloon 24 such that a substantially complete seal can be formed. Second ridge 38 can be capable of withstanding a second pressure at any point of contact between at least a portion of the outer wall 99 of sealing ridge 28 and a portion of the inner wall 11 of the bronchial lumen 2 such that a substantially complete seal can be formed. The second pressure can be substantially lower than the first pressure. Second ridge 38 can be capable of maintaining a seal between at least a portion of the outer wall 99 of the balloon 24 and a portion of the inner wall 11 of the bronchial lumen 2 against the reduced pressure along ridge 38 such that a substantially complete seal can be formed. Third ridge 53 is capable of withstanding a third pressure at the point where at least a portion of the outer surface 99 of the balloon 24 contacts a portion of inner wall 11 of the bronchial lumen 2 along ridge 53 such that a substantially complete seal can be formed. The third pressure can be substantially lower than the second pressure. Although three ridges are illustrated herein, any number of suitable ridges can be used to provide a substantially complete seal between at least a portion of the outer surface 99 of the balloon 24 with the inner wall 11 of the bronchi 49. This seal can help to retain the balloon 24 and prevent the catheter from migrating within the bronchi 49, as described above.

In yet another exemplary aspect, as illustrated in FIG. 6B, balloon 24 can comprise a tubular mesh 71. The mesh design 71 can surround at least a portion of the outer surface 99 of the balloon 24. In one aspect, the mesh design 71 can be embedded within at least a portion of the outer surface 99 of the balloon 24. Alternatively, the mesh design 71 can be free-floating about at least a portion of the outer surface 99 of the balloon 24. The mesh 71 design can be expandable and collapsible. The mesh 71 material can be made from a woven filament which can be connected to the outer surface 99 of the balloon 24. The mesh 71 material should be sufficiently strong that the balloon 24 can be retained within the mesh pattern. The mesh 71 material can comprise a plurality of fibers or filaments. In one aspect, the fibers can be inelastic, having minimal elasticity or stretch under stresses imposed upon the balloon 24 during use of the catheter. The fibers can include, but are not limited to, polyurethane, lycra, carbon fibers, ceramic fibers, metal, stainless steel, plastic, or any combination thereof. In one aspect, the mesh design 71 of the balloon 24 can be braided, woven, cross-helically wound, hexagonal or interlaced pattern, or any other suitable pattern. In one aspect, the mesh 71 configuration can be configured to have varying radial and longitudinal pitches of weave patterns. The filaments can have a rounded outer cross-sectional shape to provide a relatively smooth non-abrasive outer surface against the inner wall 11 of the balloon 24. The filaments can have varying diameters, depending on the shape and surface texture desired of the balloon 24. In one exemplary embodiment, the filaments can be between about 0.2 mm and about 0.3 mm in thickness.

When the balloon 24 is expanded radially outwardly to a predetermined configuration with a predetermined diameter, the mesh 71 pattern of the balloon 24 can contact and engage the inner wall 11 of the bronchi 49, thereby allowing a secure interference fit between the outer surface 99 of the balloon 24/mesh 71 and the inner wall 11 of the bronchial lumen 2. In the expanded state, as illustrated in FIG. 6B, and similar to the embodiment illustrated in FIG. 6A, the maximum diameter of the mesh 71 pattern can be equal to or greater than the inner diameter of the lumen 2 of the bronchi 49 in order to create a substantially complete seal of at least a portion of the outer surface 99 of the balloon 24 with the inner wall 11 of the bronchial lumen 2. The mesh 71 pattern may have a predetermined limit of expansion such that the balloon 24 can be prevented from further radial or axial expansion, regardless of the amount of pressure that is infused into the balloon cavity 9. This predetermined limit of expansion can be helpful for preventing rupture of the balloon 24 or other damage to the bronchial lumen 2. Although the balloon illustrated in FIG. 6B has a mesh 71 and ridges, in another aspect, the mesh 71 can be used with any of the catheter assemblies disclosed herein. The mesh design 71 can give the balloon 24 added strength and traction while implanted within the bronchi 49. The mesh 71 pattern can also prevent the balloon 24 from migrating within the bronchi 49, overinflating and rupturing, or damaging the bronchi 49.

Referring to FIGS. 8A and 8B, the sealing means 24 can comprise a plurality of resilient radially extending ribs 79. In one aspect, the ribs 79 can be spaced apart from each other to form an expandable and collapsible cage 30 structure. Each rib 79 has a proximal end and a distal end. The proximal end of each rib 79 is secured to at least a portion of the inner surface 18 of the balloon 24 and the outer wall of the catheter shaft 3 at the proximal end 65 of the balloon 24. In one aspect, the cage 30 can be encapsulated within the balloon 24 such that at least a portion of each rib 79 is secured to at least a portion of the inner wall 18 of the balloon 24. At least a portion of the distal end of each rib 79 can be selectively coupled to the inner wall 18 of the balloon 24. The ribs 79 of the cage 30 can be made of any suitable shape memory metal, such as, but not limited to, nitinol or nickel-titanium or other malleable materials.

Before the balloon 24 with cage 30 is inserted into a bronchial vessel, the balloon 24 and cage 30 can be in a deflated state, as illustrated in FIG. 8A. After the balloon 24 and cage 30 are inserted into the patient's bronchi 49, the balloon 24 can be expanded or inflated, as illustrated in FIG. 8B. The ribs 79 of the cage 30 can be radially expandable around the outer circumference of the catheter shaft 3 within at least a portion of the balloon 24. The cage 30 can be pre-shaped to self-expand when it is placed into a portion of the bronchi 49. In one example, the cage 30 can be collapsed when drawn within an insertion catheter or sheath. After the sheath is withdrawn, the cage 30 can be expanded to press the outer wall 99 of the balloon 24 against the inner wall 11 of the bronchi 49, thereby forming an engaging interference fit or seal with the inner wall 11 of the bronchi 49. The cage 30 configuration can help to exert a radial force or pressure against the inner wall 11 of the bronchi 49 that is sufficient to retain and anchor the balloon 24 in place. This helps to create a substantially complete seal between the outer wall 99 of the balloon 24 and the inner wall 11 of the bronchial lumen 2 and prevents the catheter from being dislodged or inadvertently pulled out of the bronchi 49.

The method of using any of the catheter assemblies illustrated in FIGS. 1 through 8B to perform dialysis treatment in a target lung region is described with reference to FIGS. 9 through 12. Before the catheter assembly 1 with sealing means 24 is inserted into at least a portion of a bronchi 49, the balloon 24 of the catheter assembly 1 can be selectively deflated, as illustrated in FIG. 5A, prior to insertion by drawing a vacuum on it (not shown).

Figure 9:
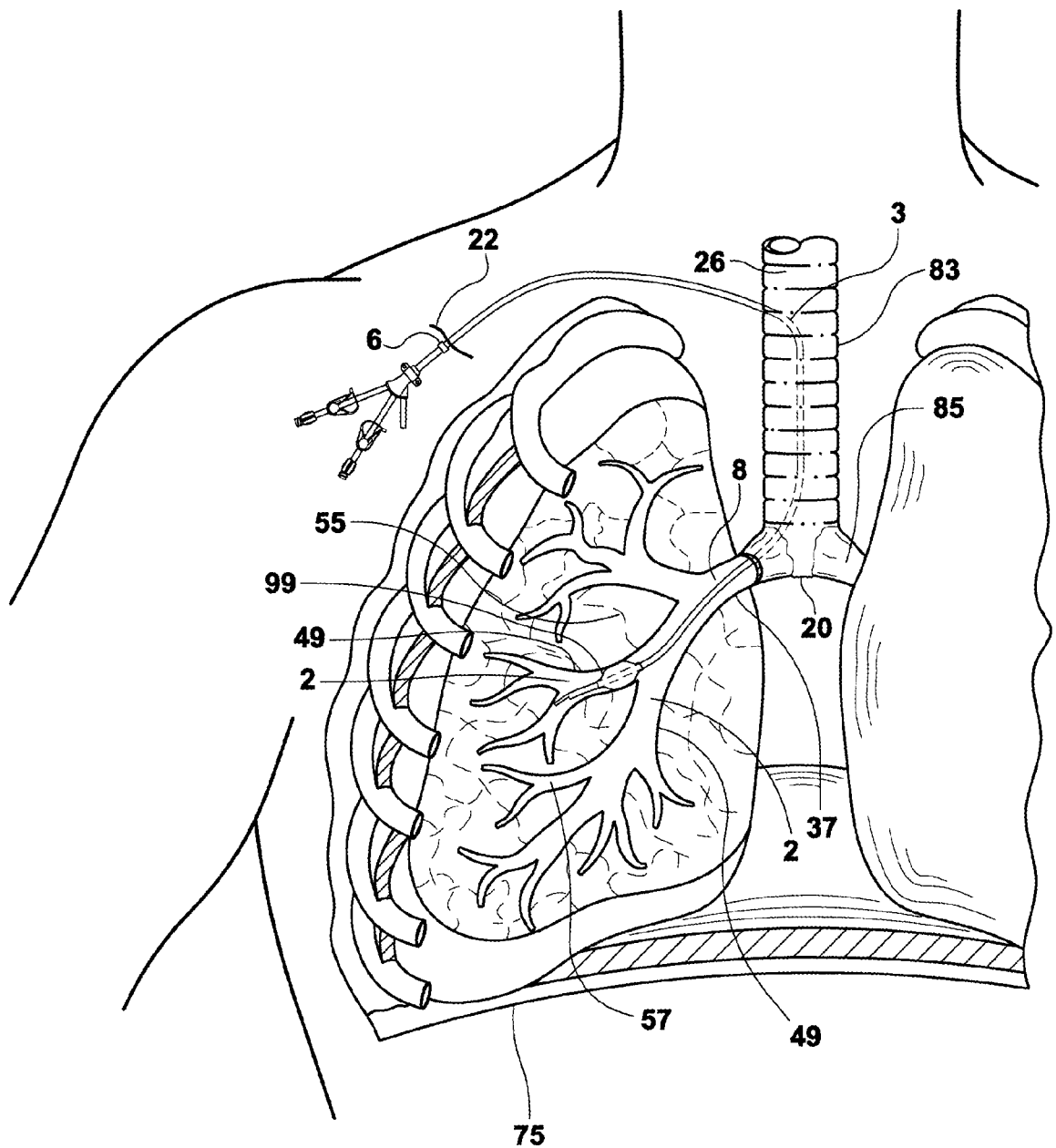
FIG. 9 illustrates a cutaway view of a human lung with the distal portion of the catheter of FIG. 1 inserted into a portion of a patient's bronchial vessel.

Referring to FIG. 9, one method of insertion and use of the catheter assembly 1 is illustrated. This method involves identifying a target lung region in a human lung into which the catheter assembly 1 described herein can be inserted. The term "lung region" refers to a defined portion of a lung. The target lung region can include an anatomical bodily opening, such as, but not limited to, a bronchi 49, which is surrounded by lung parenchymal tissue 55, as schematically illustrated in FIG. 9. The lung parenchyma 55 acts primarily as a filter. The method can further involve determining the diameter of a bronchi 49 of the target lung region, and providing an appropriately sized catheter assembly 1 described herein, for insertion into at least a portion of the bronchi 49. The diameter of the bronchi can be estimated, based on the patient's size, age, and gender. Alternatively, other various methods known in the art for determining the inner diameter of the bronchi 49 can be used. For example, the diameter can be measured using a high resolution CT scan. A loop or measuring device, such as a marked linear probe can also be used. Although bronchial diameter can vary widely among individuals, the average diameter of the bronchi for males can be about 15 mm, or 0.68 of the average tracheal width of 22 mm, and the average diameter of the bronchi for females can be about 12 mm, or 0.68 of the average tracheal width of 17 mm. All dimensions of the catheter assembly 1 disclosed herein are exemplary in nature, and can vary, depending on patient anatomy.

To insert the catheter into a patient's bronchi 49, a percutaneous incision 22 can be made in the skin of a patient's chest area below the clavicle. A needle is inserted into the incision 22 in the patient's skin and is advanced through the tissue underneath the skin. The needle is further advanced into the thoracic cavity and further toward the trachea 83. The trachea 83 can then be palpated and stabilized with the thumb and forefinger of a practitioner's hand, and the needle can be slowly advanced in a horizontal direction towards the trachea 83 with a practitioner's remaining hand while directing the needle straight towards the midline of the trachea 83, in order to enable penetration of the lumen 26 of the trachea 83. When the needle contacts the wall of the trachea 83, the needle can be advanced a short distance up or down in order to find and penetrate a ligament between two cartilaginous tracheal rings. When the needle penetrates the trachea 83, a distinct pop can usually be felt. After penetration of the trachea 83, the needle can be carefully held in position within the lumen 26 of the trachea 83, to prevent it from prematurely backing out of the airway. If the needle is advanced too far within the lumen 26 of the trachea 83, the dorsal wall of the trachea 83 can prevent the catheter from passing through the needle.

Once the needle is correctly positioned within the lumen 26 of the trachea 83, the needle can be slowly turned from a horizontal position to a 45 degree angle, pointing bevel-down towards the carina 20, or cough center, positioned at the junction of the left and right bronchi. The trachea has a series of cartilaginous semi-rigid rings, described above, that help to maintain the tracheal airway. Between each of the cartilaginous rings is a thin, soft tissue. As schematically illustrated in FIGS. 9 through 12, the trachea 83 divides into two branches, which become the bronchi of the lungs, a right primary bronchus 37 and a left primary bronchus, that each provide direct air flow to the right and left lungs, respectively. The bronchi are connected to the lungs. The lungs are large, paired, spongy, elastic organs, which are positioned in the thoracic cavity. The lungs are in contact with the walls of the thoracic cavity. The right lung comprises three lobes, and the left lung comprises two lobes. Each of the left and right lungs is covered with a pleural membrane or sac. The pleural space is the space surrounding the lungs. The thoracic cavity is normally a closed system, and air cannot enter or leave the lungs except through the trachea. Healthy lungs have a large surface area for gas/air exchange.

Each of the primary bronchi 37, 85 divides into bronchial vessels 49, 28, which are defined by a lumen through which fluids and air can flow to and from the lung. The lobar bronchi feed fluid directly to a respective lung lobe, and each lobar bronchi divides into bronchial vessels that are comprised of segmental bronchi, which provide air flow to the bronchopulmonary segments. The bronchi branch into bronchioles, and the bronchioles lead to alveolar sacs which include multiple alveoli separated by alveolar walls for the exchange of oxygen and carbon dioxide. The bronchial arteries supply blood to the bronchi and connective tissue of the lungs. They travel with and branch with the bronchi, ending about at the level of the respiratory bronchioles. They anastomose with the branches of the pulmonary arteries, and together, they supply the visceral pleura of the lung in the process.

After a needle is inserted into the trachea 83, a guide wire is inserted into the trachea 83 through the inserted needle. In one aspect, the guide wire can be about 0.035 inches in overall diameter, although other lengths and diameters are possible. The needle is then withdrawn, with the guide wire being left in place. A dilator/sheath assembly can then be placed over the guide wire and advanced to a position inside the trachea 83. Once the guide wire and the dilator/sheath assembly are advanced to the trachea 83, the dilator is removed, and the distal portion 14 of the catheter assembly 1 is inserted into the sheath, back loaded over the proximal end of the guide wire, and advanced via tunneling beneath the skin until the cuff 6 is positioned just beneath the skin. The guide wire is used to control the path of the catheter shaft 3, which tracks over the guide wire, and ensures that the catheter shaft 3 properly negotiates the path to the target lung region. The distal portion 14 of the catheter assembly 1 is introduced into the trachea 83 via the introducer sheath and over the guide wire and advanced through the trachea 83 into the right bronchus 37 and further into the right bronchi 49, being careful to avoid the carina 20. As the distal portion 14 of the catheter shaft 3 is advanced through the trachea 83, the catheter can conform to the shape of the trachea until the distal portion 14 of the catheter assembly 1 is located at the target lung location of the bronchi 49, as illustrated in FIG. 9. Passage of the catheter shaft 3 through tortuous bronchial anatomy can be further facilitated by using a steerable distal end portion 14 of the catheter shaft 3 that can be controlled remotely. The catheter assembly 1 can be positioned such that the distal tips 13, 15 of the catheter are located at the proper position within the bronchi 49, as confirmed under ultrasound or fluoroscopy. Markers positioned along the catheter shaft 3 can be used to indicate the desired depth of the catheter shaft 3 within the right bronchi 49. In one aspect, the proximal portion 65 of the inflated balloon 24 can be positioned approximately 10 mm past the beginning of the right bronchus 37 into the right bronchi 49. The guide wire can be configured to extend only a minimally short distance from the distal portion of the catheter shaft 3 to minimize the chance of puncturing the lungs. Although the distal portion 14 of the catheter assembly 1 is shown inserted into the right bronchi 49, alternatively, the distal portion 14 of the catheter can be inserted into the left bronchi. However, it is more difficult to insert the catheter into the left bronchial passage compared to the right bronchial passage because the left bronchial passage is slightly smaller and branches at a slightly greater angle from the main trachea 83 compared to the right bronchial vessel. The right bronchi 49 is better suited for catheter insertion because it is wider, more vertical, 5 cm shorter than the left bronchi, and is positioned at a 20-30 degree angle compared to the left bronchi, which is narrower, longer, and more angular, having a 40-60 degree angle, compared to the right bronchi.

In one aspect, the catheter assembly 1 can be laparoscopically inserted into a target lung region. This technique involves the use of a laparoscope that can be manually advanced in parallel with the catheter shaft 3. The use of the catheter assembly 1 with a laparoscope allows a clinician to gain visual and functional access to the interior of a patient's lungs. Optionally, visualization of the progress of the distal tips 13, 15 of the catheter shaft 3 can be provided by, but is not limited to, a bronchoscope, x-ray, ultrasonic, radiographic, computed tomography (CT), or other video-assisted techniques or visualization systems to provide supplemental visualization during the insertion procedure. Video-assisted techniques can involve using a small video camera that is introduced into the patient's chest via a scope. A practitioner can view the instruments that are being used along with the anatomy into which the catheter is being inserted. The camera and instruments can be inserted through separate holes in the chest wall, also known as "ports". Fluoroscopy can be used to visualize and ensure that the guide wire is not dislodged while the catheter shaft 3 is advanced over the guide wire. The guide wire and the sheath can then be removed, leaving at least a portion of the distal portion 14 of the catheter assembly within the bronchial vessel 49.

After at least a portion of the distal portion 14 of the catheter assembly 1 is confirmed as being located at the proper position within the lumen 2 of the right bronchi 49, at least a portion of the bronchi 49 of the target lung region can be bronchially isolated. This is accomplished by inflating the balloon 24 of the catheter assembly 1 within a portion of the bronchi 49 to form a substantially complete seal between a portion of the outer wall 99 of the balloon 24 and a portion of the inner wall 11 of the bronchial lumen 2. To inflate the balloon 24, fluid, gas, or air can be infused into inflation port 63, through lumen 43, and into the balloon 24 through opening 69 using a syringe or vacuum device that can be attached to the inflation lumen port 63 at the proximal end of the catheter assembly 1, as described above. In one aspect, an infusion of approximately 0.5 to 10 mL of air can be sufficient to inflate the balloon 24 such that it can cause occlusion across the diameter of an anatomical bodily opening, such as, but not limited to, the right bronchi 49. As air, gases, or fluids are infused into the inflation port 63 through inflation lumen 43, the diameter of the balloon 24 can expand so that at least a portion of the outer surface 99 of the balloon 24 can engage at least a portion of the inner wall 11 of the bronchi 49, thereby forming a substantially complete seal of the lumen 2 of the bronchi 49. This is important because the bronchial lumen 2 can become constricted or otherwise change shape during inhalation, exhalation, or coughing. If the balloon 24 is not secured properly, when a patient coughs, pressure can build up behind the catheter, which can lead to migration or expulsion of the balloon catheter from the bronchial lumen 2. The bronchial lumens expand when air is inhaled, which can cause the catheter to migrate in the distal direction, and can result in the device being pushed further into the lung. This can lead to a less secure retention of the device in the bronchial lumen 2. However, the seal created by the inflated balloon 24 helps to isolate or seal off at least a portion of the lung to create a treatment chamber that is located distally of the point where a portion of the outer surface 99 of the balloon 24 contacts a portion of the inner wall 11 of the bronchial lumen 2 for dialysis treatment.

After the balloon 24 is inflated, the position of the balloon 24 can be inspected under fluoroscopy and adjusted, if necessary, so that the inflated balloon fills the bronchial lumen 2 without herniation into the lumen 26 of the trachea 83. The balloon inflation volume can also be noted, and the inflation volume can be between about 5 ccs and about 10 ccs. The inflation volume will depend on the size of the catheter, the size of the bronchial vessel in which the catheter assembly is to be placed, and the like. If the balloon 24 is mis-positioned, the balloon 24 can be deflated, if necessary and then reinflated when appropriate. The balloon 24 should fill a majority of the bronchi 49, such that at least a portion of the lumen 2 can be substantially occluded. Likewise, if the distal tip of the catheter shaft 3 is not positioned properly, the catheter can be re-positioned by inflating the balloon 24 such that it can be used to position the distal tip of the catheter in the proper location. The methods of insertion described herein are advantageous because the catheter assembly 1 does not have to be inserted via the mouth or nose, thereby leaving the patient free to breathe in an unobstructed manner. The substantially
complete seal between the outer surface 99 of the balloon 24 and the inner wall 11 of the bronchi 49 allows a user to be better able to infuse a dialysate fluid into the treatment chamber within the lungs distally of catheter tips 13, 15. Other fluids can be infused along with, or separately from, the dialysate fluid, to reduce or eliminate mucus production or for other medicinal purposes.

After the catheter is properly positioned within the lumen 2 of the bronchial vessel, dialysate can be infused into the patient from an infusion pump (not shown). Fluid can be withdrawn from the patient's venous system and transported through aspiration lumen 39, illustrated in FIG. 2A, of tube 5 at opening 15, through extension tube 21 and out opening 27. Aspiration of the blood through aperture 15 of tube 5 can be accomplished by drawing a vacuum or negative pressure, causing the blood to be drawn through the catheter. Dialysate can then be infused into to the patient's lung through opening 27 of luer connector 25 on extension tube 19 which is connected to the infusion pump, into infusion lumen 36 of infusion or venous tube 7 with infusion lumen 36 (FIG. 2A), under pressure, through distal opening 13, and out through the distal end 13 of the catheter assembly 1 into the patient's lung. Although the lumens 39 and 36 have been designated as aspiration and infusion lumens, respectively, the functions of these lumens can be reversed, if desired.

The dialysis treatment process can be repeated several times using the same catheter. A predetermined bolus of dialysate fluid can be infused into the patient's lung through lumen 36 at a predetermined temperature, volume, and infusion rate. In one aspect, once adequate time has elapsed, a new bolus of dialysate can be infused into the lung. Typically, about 150 mls of dialysate solution can be infused into a patient's lungs during treatment. The infused dialysate or solution is maintained for about five to ten minutes and then discharged. The procedure can be repeated continuously as necessary to achieve the desired reduction of contaminants.

In one exemplary aspect, the catheter described herein can be used with any suitable type of dialysate. The dialysate solution can be a in a liquid form. The composition and dosage of the dialysate solution can differ depending on the age, body weight, and conditions of the patient, and the manner and frequency of administration. The concentration of each component in the dialysate can be tailored to the individual patient. The dialysate solution can comprise sodium chloride as a main, and most important component. During dialysis, the goal is to remove the exact amount of sodium that has accumulated between dialysis sessions. Sodium and water gains obtained during the preceding interdialytic interval are disposed of, while no significant changes are made to the plasma sodium concentration. If 1 L of dialysate solution is used during a dialysis session, approximately 135 mmol of sodium will be removed. The lower volume of dialysate used in the lung compared to peritoneal dialysis (2 L to 3 L) can reduce the fluid loading normally encountered when filling the abdomen with large volumes of dialysate.

Electrolytes such as potassium, calcium, and magnesium are also important components of a dialysate solution. Thus, potassium chloride, calcium chloride, and magnesium chloride can be added as minor components. Other components can be added as well, such as, but not limited to, sodium bicarbonate or acetate, potassium, and calcium. Sodium bicarbonate can be used as a pharmaceutically acceptable alkalizing agent or alkalizing salt or buffer. Alternatively, sodium acetate can be used, which metabolizes in the bloodstream to sodium bicarbonate. In one exemplary embodiment, a sample dialysate composition is provided in Table I below, although any suitable type of dialysate solution can be used in the method described herein, and the concentrations of the constituents may be varied, as necessary. Thus, the dialysate solution can contain a therapeutically effective amount of any of the components described herein, such as, but not limited to, sodium, potassium, chloride, calcium, magnesium, bicarbonate, acetate, and dextrose. The term "therapeutically effective amount" as used herein refers to that amount of the compound being administered which will relieve to some extent one or more of the symptoms of the disorder being treated. As used herein, "mEq/L" refers to the concentration of a particular dialysate component (solute) present in proportion to the amount of water present, or the mill-equivalents of solute per liter of water.

TABLE 1

| Constituent | Concentration Range | |
|---|---|---|
| NaCl (Na+) | 125-150 | mEq/L |
| KCl (K+) | 0-5 | mEq/L |
| HCl (Cl−) | 80-130 | mEq/L |
| CaCl$_2$•2H2O (Ca+) | 0-5 | mEq/L |
| MgCl$_2$•6H$_2$O (Mg+) | 0-3 | mEq/L |
| CH$_3$COOH | 0-37 | mEq/L |
| NaHCO$_3$ | 15-50 | mEq/L |
| Dextrose (glucose monohydrate) | 0-4250 | mEq/L |
| H$_2$O | 1 | L |
| Icodextrin | 4.0% | w/v |

In one aspect, sodium can be present in the dialysate solution in the amount of about 137 mEq/L. The potassium concentration in the dialysate solution can be between about 1.5 mEq/L to about 2.5 mEq/L. More particularly, the potassium concentration can be about 2.0 mEq/L. The chloride concentration can be about 109 mEq/L. The calcium concentration can be between about 2.5 mEq/L and about 3.25 mEq/L, and more particularly, about 3.0 mEq/L. The magnesium concentration can be between about 1.25 mEq/L and about 1.5 mEq/L, or more particularly, about 0.75 mEq/L. In one aspect, the acetate concentration can be between about 0 mEq/L to about 8 mEq/L, or more particularly, about 4.0 mEq/L. The bicarbonate concentration can be about 33 mEq/L. Icodextrin, a colloid osmotic agent which acts as an adhesion reduction solution, can be present in the dialysate solution in the amount of about 4.0% w/v. The balance of the dialysate solution is water. The osmotic pressure of the dialysate can be adjusted to between about 300 and about 700 mOsm/L. The final pH of the dialysate can be between about 7.1 and about 7.4. The final dialysate solution can have a low osmolarity and is preferably iso-osmolar, or isotonic.

The dialysate solution can also comprise at least one excipient or additive, such as, but not limited to, a binder, a disintegrant, a lubricant, a coloring agent, a sweetening agent, and a flavoring agent. Other additives that can be added include, but are not limited to, urea, phosphorus, ethanol, iron, citric acid or citrate, lactates, gluconates, glucose as an osmotic agent, antimicrobial peptides, starch, kaolin, microcrystalline cellulose, and various sugars in differing concentrations, such as, but not limited to dextrose or fructose as an osmotic agent, or sucrose. Other additives can include propanol, simple syrup, liquefied gelatin, hydroxypropylcellulose, hydroxypropyl starch, methyl cellulose, ethyl cellulose, shellac, calcium phosphate, polyvinyl pyrrolidone, sodium arginate, sodium hydrogencarbonate, calcium carbonate, sodium lauryl sulfate, monoglyceryl stearate, vitamins, and lactose. Other viscosity modifiers, which can increase the viscosity of the dialysate solution, can be added, such as, but not limited to, carboxymethyl cellulose (CMC), sorbitol, or dextran. CMC has a high viscosity, is non-toxic, and is non-allergenic. Lubricants can be added, which include purified talc, stearic acid salts, borax, and polyethylene glycol.

After dialysis is performed within at least a portion of the lung, the catheter can remain in place within a patient's lung for as long as treatment is necessary. Thus, in summary, the method of using any of the catheter assemblies described in FIGS. 1 through 12 can involve determining the dimension of a bronchial vessel of a target lung region; providing a catheter assembly having a sealing means, as described herein; deflating the means for sealing so as to allow it to be inserted into the lung; inserting the catheter into a bronchial vessel; advancing the means for sealing to a position within a portion of the bronchi, inflating the means for sealing until the means for sealing substantially occludes at least a portion of the bronchial vessel; infusing a dialysate solution into a portion of the lung through the distal end of the catheter through an infusion lumen; deflating the means for sealing; and removing the catheter.

Figure 10:
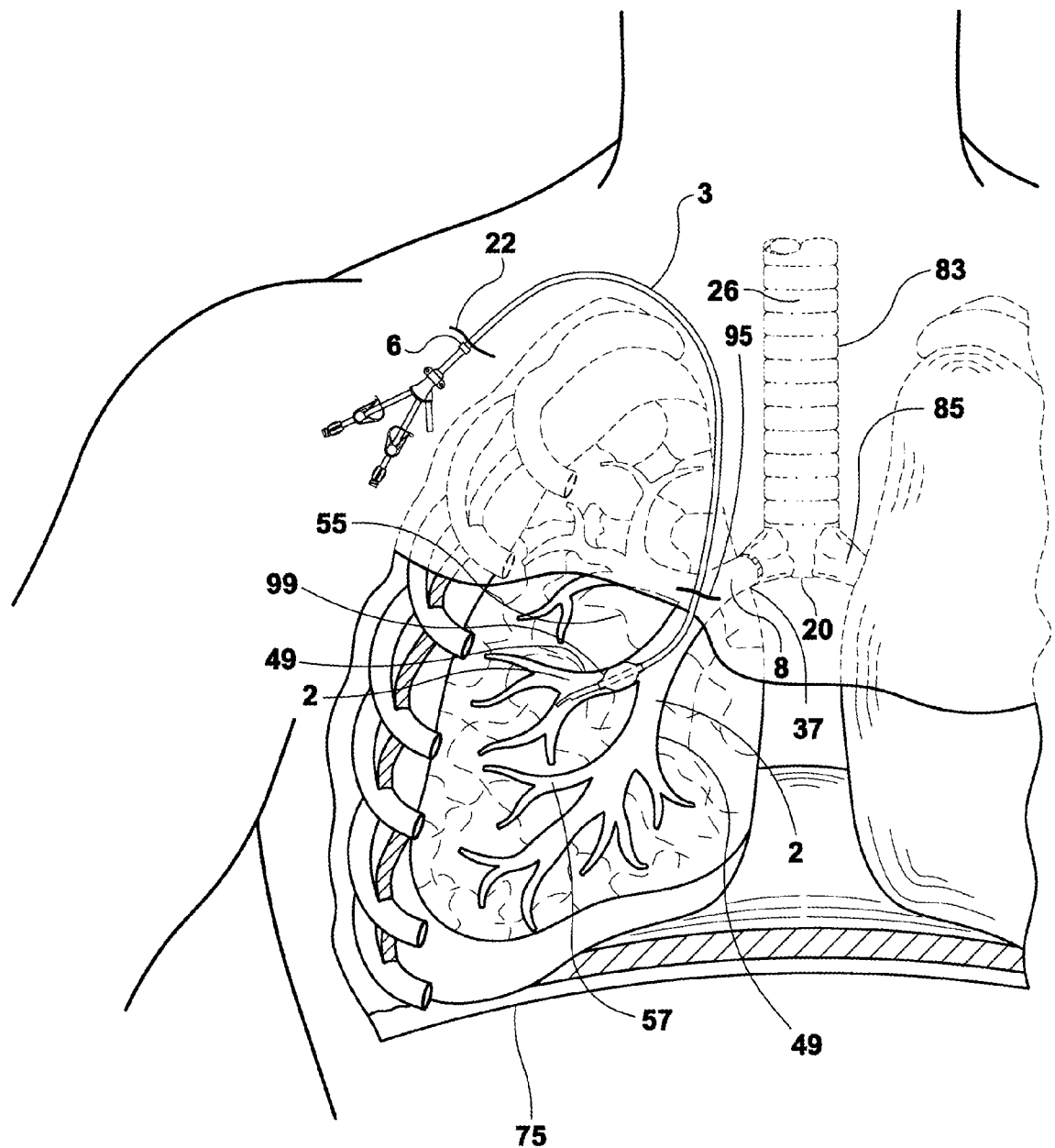
FIG. 10 illustrates a partial cutaway view of a human lung with the distal portion of the catheter of FIG. 1 inserted into a portion of a patient's bronchial vessel.

Referring to FIG. 10, an alternative method of inserting the catheter assembly 1 is illustrated. In this method, the catheter assembly 1 can be inserted directly into the bronchi of a patient's lung using the same insertion procedures outlined above. Instead of tunneling the catheter to the trachea 83 from the incision point 22 below the clavicle, as described above, the catheter is tunneled through the skin to a point directly above the bronchus 37. An incision 95 is then made through the lung tissue or parenchyma 55 into the bronchial wall. This incision can be made using a substantially rigid tapered sharp or pointed tip cutting catheter that can act as a puncturing element. Alternatively, the bronchial wall can be punctured using a stiff guide wire delivered via a lumen of the catheter assembly 1. In yet another aspect, RF or laser energy can be delivered through the distal tip of the catheter to make an incision in the bronchial wall. The distal portion 14 of the catheter assembly 1 can then be advanced through the bronchus 37. As the distal portion 14 of the catheter shaft 3 is advanced through the bronchi 49, the catheter can conform to the shape of the bronchi 49. The wall of the bronchi is cartilaginous and enforced with smooth muscle which makes it strong, and therefore, ideal for securely holding an inserted catheter tube. Dialysate solution is then infused into the target lung region using the catheter assembly 1, as described above.

Figure 11A:
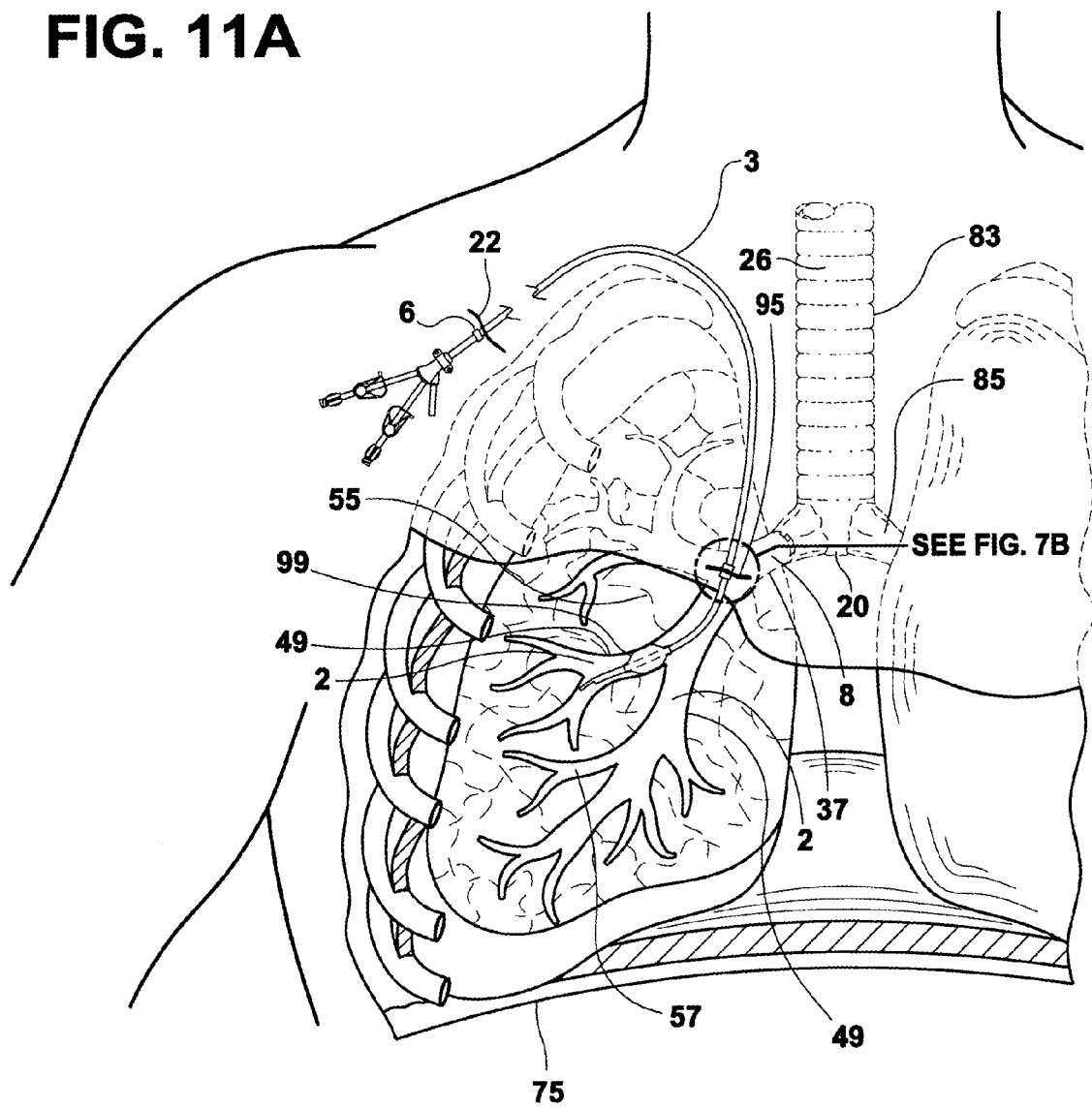
FIG. 11A illustrates a partial cutaway view of the distal portion of the catheter of FIG. 1 being inserted into a portion of a patient's bronchial vessel.
Figure 11B:
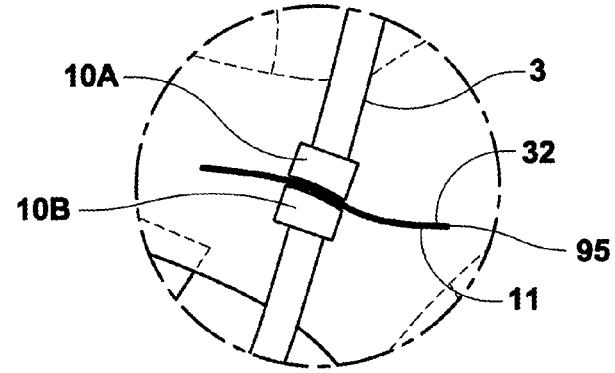
FIG. 11B illustrates an enlarged view of a portion of the catheter shaft being inserted into a portion of a patient's bronchial vessel.

FIGS. 11A and 11B illustrate a variation of the method of insertion and use of any of the catheter assemblies described in FIGS. 1 through 8B. This method involves inserting the catheter directly into the bronchi 49 through the bronchial wall as described above. Additionally, before the catheter is inserted into the bronchi, a means for securing the catheter shaft 3 in place can be used in order to provide a non-traumatic anchoring system for the patient. The means for securing can comprise at least one collar. The catheter shaft 3 can be pre-assembled with the collars 10A, 10B attached to a portion of the outer surface of the catheter shaft 3. Collars 10A, 10B can be positioned on either side of the bronchial wall to secure the catheter shaft 3 within a portion of the bronchi 49 so that the catheter does not become dislodged. In one aspect, the collars 10A and 10B can provide a substantially complete seal of the catheter shaft 3 and help to stabilize the shaft 3 between the outer surface 32 of the bronchi 49 and inner wall 11 of the bronchi 49 at the point where the catheter is inserted into the bronchi 49 to help secure the catheter in place and to avoid any leakage. In one aspect, the bronchial wall thickness can be between about 0.1 mm and about 5 mm. The collars 10A, B can be adjusted in size depending on the thickness of the bronchial wall. Each collar 10A, B can have a diameter of between about 3 mm and about 7 mm.

Each collar 10A, 10B can have at least an inner surface and an outer surface. The inner surface of the collars 10A, B can be disposed around and engaged with at least a portion of the circumference of the outer surface 99 of the catheter shaft 3. Each collar 10A, B can have an annular shape that can be configured to restrict the circumference of the catheter shaft 3 that passes therethrough. In one aspect, each of the collars 10A, B can have various shapes, such as, but not limited to, a disc having a circular, or curved shape. The collars 10A, B can also be oval or any other suitable shape. In one aspect, the dimensions of the collars 10A, B can be identical to the shape of cuff 6. The collars 10A, B can be spaced from each other from about 1 mm to about 5 mm along the longitudinal length of the catheter shaft 3. In one aspect, the collars 10A, B can be hollow. Alternatively, the collars 10A, B can be solid. In one aspect, the collars 10A, B can be flexible. Each collar 10A, B can have an orifice (not shown) through which a portion of the catheter shaft 3 can be inserted.

In one aspect, the inner diameter of the collars 10A, B can be smaller than the outer diameter of the catheter shaft 3 such that an interference fit can be formed between the outer surface of the catheter shaft 3 and the inner surfaces of the collars 10A, B. This interference fit provides a suitable seal and sufficient friction to prevent the collars 10A, B from moving once they are properly positioned. The collars 10A, B can be flexible and can be made of a Dacron® material or any other suitable material. Dacron® material allows the cuffs to integrate with the body tissue to form a scar tissue to seal the catheter at its point of entry. Alternatively, collars 10A, B can be comprised of a biocompatible polymeric material, such as, but not limited to, silicone, or any other suitable material, such as a flexible plastic material similar to the catheter tube.

Each collar 10A, B can be slidably coupled to at least a portion of the outer surface of the catheter shaft 3 such that they are adjustable along the length of the catheter shaft 3 during implantation. This allows a user to position the collars 10A, B at a desired location along the catheter shaft 3 where the catheter shaft 3 will be inserted into the bronchi 49. Once the collars 10A, B are moved along the catheter shaft 3 to a desired position, the position of the collars 10A, B can be fixed. Alternatively, the collars 10A, B can be fixed along the catheter shaft 3 at a predetermined position. When the catheter shaft 3 is inserted into bronchi 49, the inner surface of collar 10B is positioned just inside bronchi inner wall 11 such that it is positioned generally parallel to and abutting up against the inner surface 11 of the bronchi 49. The inner surface of collar 10A abuts the outer wall 32 of the bronchi 49, as illustrated in FIG. 11B. In use, first collar 10A can be disposed on one side of the incision 95, and second collar 10B can be disposed on the other side of the incision 95, thereby forming an elastomeric seal with the bronchial wall.

Although not illustrated, collars 10A and 10B can be capable of being joined together after the catheter is inserted into a patient, such that after the catheter is secured within the bronchial lumen 2 with collar 10B, collar 10A can be cinched distally along the outer surface of the catheter shaft 3 toward the outer wall 32 of the bronchi 49. This can help to create a fluid tight seal within the bronchi 49. In one aspect, although not illustrated, collars 10A, 10B can comprise at least one integrally formed flange that can be connected to a portion of the collars 10A, B and can be inserted into the bronchi 49 such that the flange engages a portion of the inner wall 11 of the bronchi 49 and forms a seal with the inner surface of the bronchial wall 11. The collars 10A, B can have an inner flange that is used to secure the catheter shaft 3 to the inner wall 11 of the bronchi 49 and an outer flange that is used to secure the catheter to the exterior wall 32 of the bronchi 49. The flanges can be made of a flexible or malleable material, such as, but not limited to, Nitinol.

The method of using a catheter involving collars 10A, 10B comprises identifying a target lung region; providing any of the catheter assemblies described herein having at least one collar, as described above; determining the diameter of a selected bronchial vessel within the target lung region; inserting at least a distal portion of the catheter assembly into at least a portion of the bronchial vessel; adjusting at least one of the first and second collars to a predetermined position on the catheter shaft 3, if necessary; and infusing a dialysate solution into the target lung region, as described above. The advantage of using collars 10A, B is that once the collar 108 is inserted inside of a portion of the bronchial wall 11, the collars 10A, B provide a relatively minimally invasive means of securing the distal portion 14 of the catheter assembly 1 in place at the bronchial incision point 95. Collars 10A, 10B can thereby provide an effective sutureless anchoring means for securing a portion of the outer surface of the catheter shaft 3 at the incision site 95 and preventing migration and infection of the catheter shaft 3 at the insertion site 95. This method allows the insertion of the catheter shaft 3 without the need for a suture.

Figure 12:
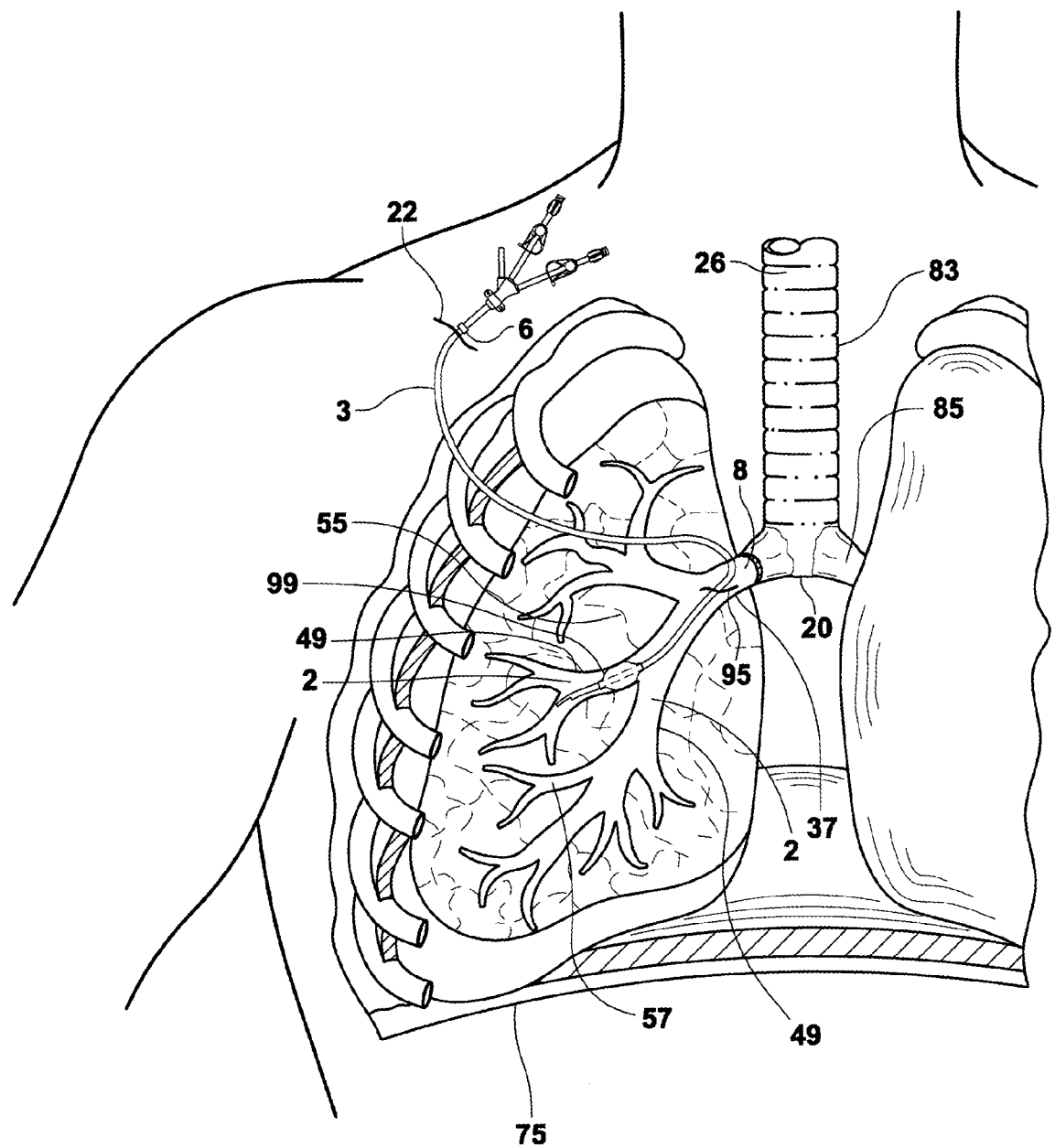
FIG. 12 illustrates a cutaway view of the distal portion of the catheter of FIG. 1 being inserted into a portion of a patient's bronchial vessel.

Referring to FIG. 12, another exemplary method of insertion and use of the catheter is illustrated. In this method, any of the embodiments of the catheter described herein can be inserted into the interpleural space, or the space surrounding the lungs, and further into the intercostal space, or the space between any two ribs of a patient. At least one intercostal space can located by a practitioner. For example, the second intercostal space (the area between the second and third ribs, counting from the top) or the third intercostal space (the space between the second and third ribs, counting from the top) can be located, which can be accomplished by a practitioner's fingers feeling the ribs on either side of the relevant intercostal space. The patient's skin is then cleaned with betadine or another type of antiseptic. The appropriate intercostal space is then identified again in the mid-clavicular line, an imaginary line perpendicular to the ribs.

A needle is then inserted into the pleural space, which is the space surrounding the lungs, over the top of the second or third rib into the pleural space on the right side of the chest, if the right lung is targeted, as described above. This will help to avoid the blood vessels and nerves which run under the bottom of the rib. When the needle is inserted into the patient, the practitioner may feel a "pop" as the needle pierces the outside pleural membrane or parietal pleura, then the visceral pleura, and enters the chest cavity after the chest cavity has been penetrated, after which a hiss of escaping air may be heard. Air is then aspirated, if necessary.

A guide wire is inserted into the needle and into the pleural space, and the needle is then removed. The catheter is inserted over the guide wire. An incision is then made parallel to the ribs over the guide wire of between about 1 cm and 1.5 cm in length, depending on the size of the catheter and the pleural cavity. The catheter is then delivered into the pleural cavity over the guide wire, the guide wire is removed, and the catheter is advanced to the bronchus and further into the bronchi 49, where it is inserted through insertion site 95, as described above. The chest incision 22 is closed, and the catheter is then secured in place. This method of inserting the catheter is advantageous because this method is very rapid, vascular structures are avoided, and the positioning of the catheter can be more easily controlled compared to the other insertion methods described herein. This method also allows patients to lie on their backs and allows drainage to be increased.

Figure 13:
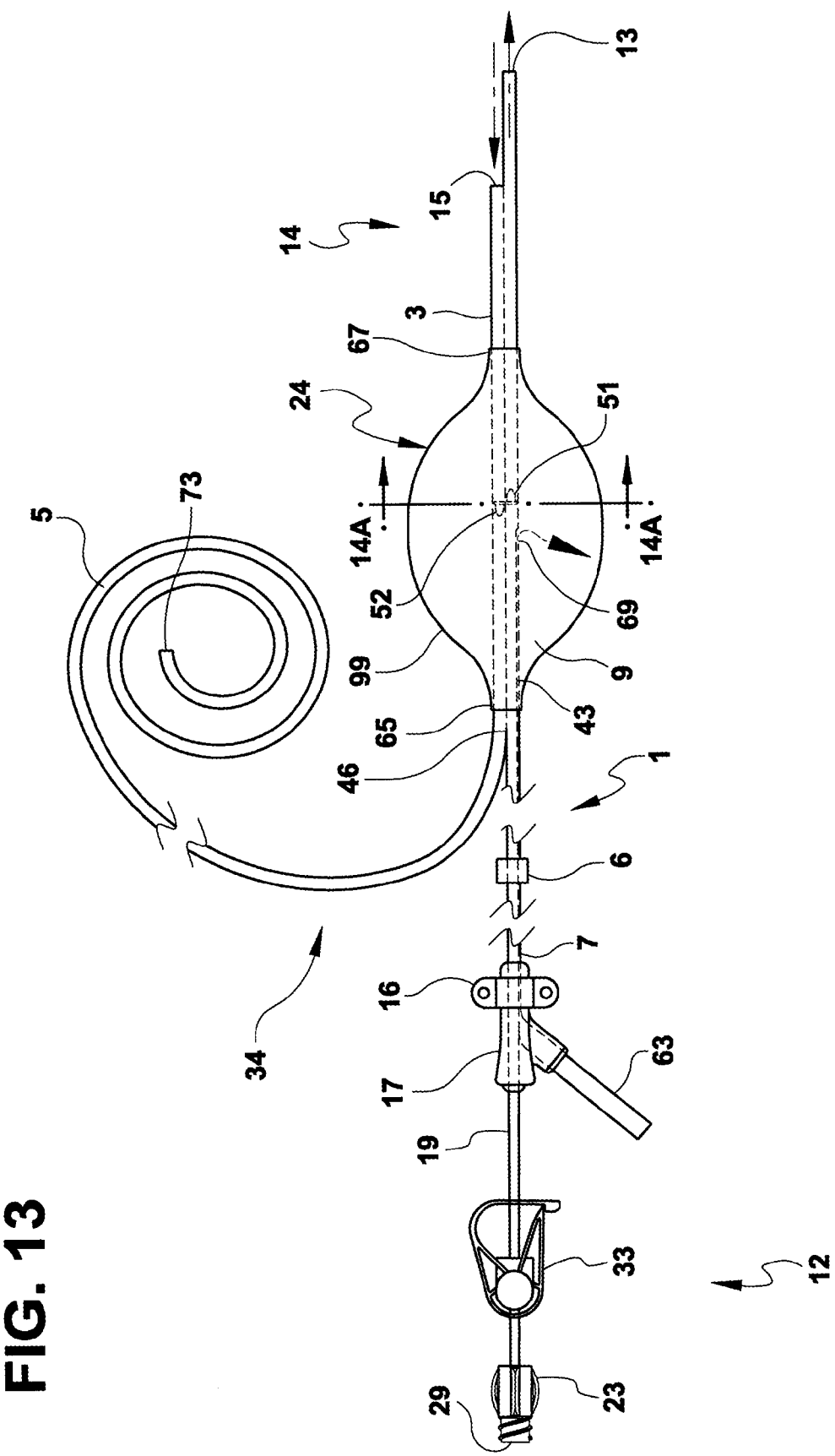
FIG. 13 illustrates a plan view of an additional embodiment of the catheter of the present invention.

Referring to FIG. 13, another embodiment of a catheter assembly 1 is described herein. This embodiment is similar to that illustrated in FIGS. 1 through 12, except the catheter shaft 3 can comprise at least one unidirectional check valve. In one aspect, the catheter shaft 3 can comprise two valves 51, 52. Valves 51, 52 can be positioned within and coupled to at least a portion of the lumens 36, 39, respectively. The valves 51, 52 can be flexible and elastomeric and can be configured to be disposed within a portion of the lumens 36, 39 such that fluid must flow through the valves 51, 52 in order to flow through the lumens 36, 39. The valves 51, 52 can be positioned at various locations within the lumens 36, 39 along the catheter shaft 3. In one exemplary embodiment, the valves 51, 52 can be positioned at the distal portion 14 of the catheter shaft 3. Although one valved catheter embodiment is described herein, it is contemplated that other bidirectional valve configurations could be used, such as, but not limited to, those described in U.S. Pat. No. 5,112,301, incorporated herein by reference in its entirety.

The proximal portion of the catheter tube 7 has a proximal opening or tip 73. The proximal tip 73 of tube 7 is configured to be non-traumatic such that when it is inserted into a patient's bladder, it does not cause discomfort to a patient. Tube 7 of the catheter shaft 3 can have a longer length compared to catheter tube 5, such that, in its unstressed configuration (not shown), the proximal opening 73 extends proximally of the proximal end of the catheter assembly 1. Tube 7 is joined to tube 5 from the distal end of the catheter to point 45, where catheter tubes 5 and 7 separate from one another. In one aspect, the length of the catheter tube 7 can be between about 50 cm and about 120 cm. More particularly, the length of the catheter tube 7 can be about 80 cm. In one exemplary aspect at least a portion of the catheter shaft 3, such as, but not limited to the proximal portion of catheter tube 7, can be coated with silicone spray or jelly for additional lubrication before the catheter is inserted into the bladder of a patient in order to facilitate better insertion and advancement of the distal portion 14 through the lung and into the abdominal cavity, as described herein. At the proximal end of the catheter assembly 1, the catheter can comprise one extension tube 19 instead of two extension tubes. In one exemplary aspect, the proximal portion of the catheter tube 7 can comprise at least one retaining means, such as, but not limited to a flange or at least one collar similar to collars 10A, B, described herein. The purpose of the retaining means can be to secure at least a portion of the catheter shaft 3 within a portion of the bladder to help prevent the catheter from becoming dislodged during use.

Figure 14A:
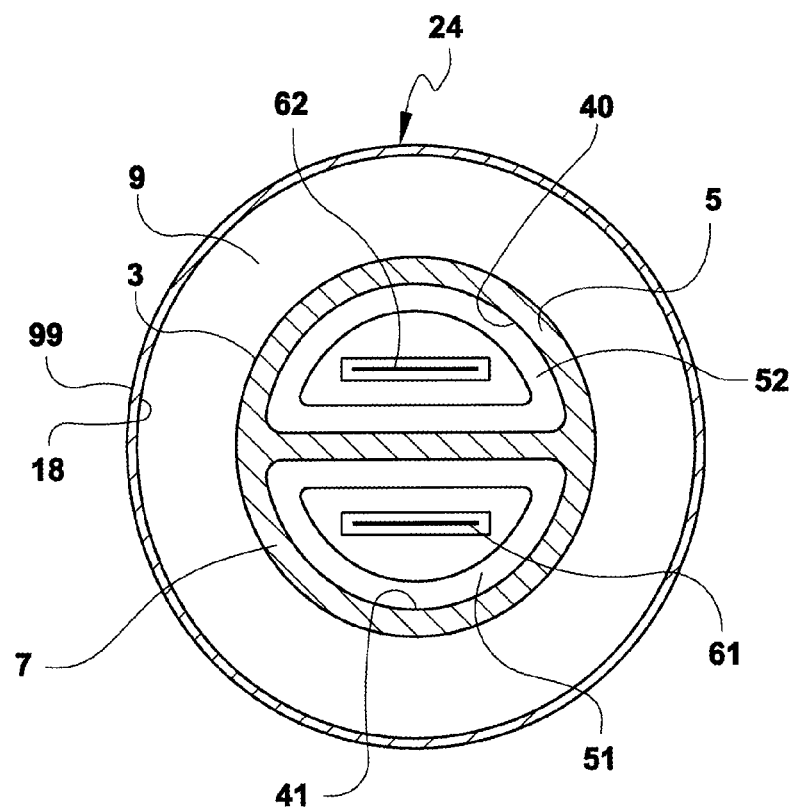
FIG. 14A illustrates a cross-sectional view of the catheter of FIG. 13 along line 13A-13A.
Figure 14B:
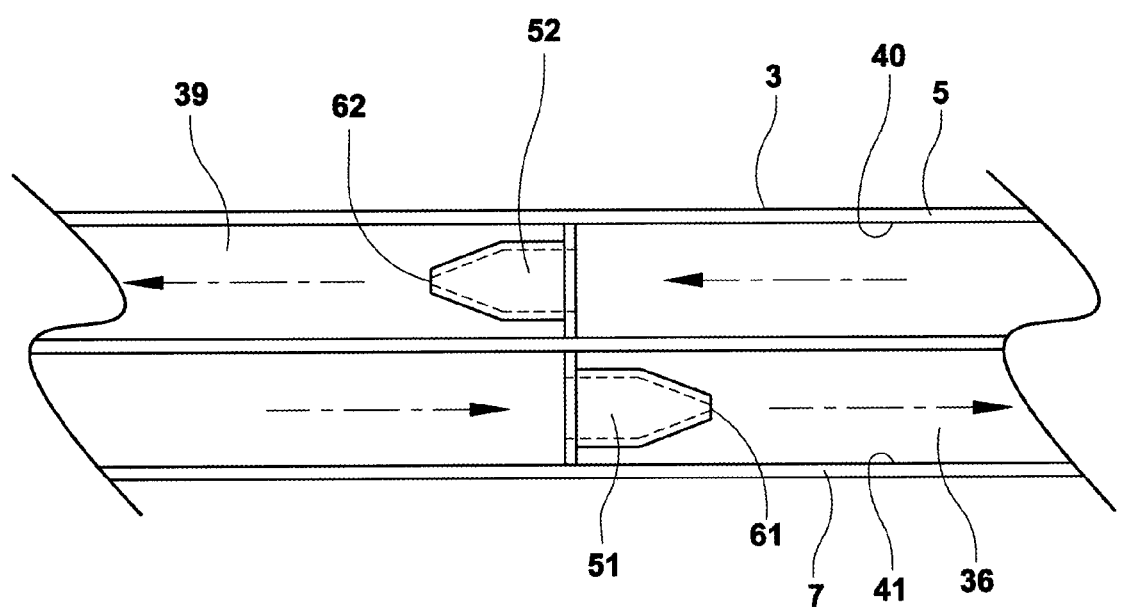
FIG. 14B illustrates a longitudinal sectional view of a portion of the catheter shaft of FIG. 13 along line 13B-13B.

Referring to FIGS. 14A and 14B, the valves 51, 52 can be selectively coupled to at least a portion of the inner walls 41, 40 of lumens 36, 39 using any suitable molding, adhesive, or bonding process. In one aspect, the valves 51, 52 can be minimally invasive and integral with lumens 36, 39 of the catheter shaft 3. In one aspect, the valves 51, 52 can be made of any suitable biocompatible material, such as, but not limited to, silicone, thermoplastic elastomers, urethane, etc.

Valves 51, 52 can have a duckbill valve configuration in which each valve has a body, a proximal end and a distal end, and a generally tubular base. The body of the valves can be generally cylindrical in shape along a portion of the body. The base can be tubular with an outer diameter that fits within the lumens 36, 39 of the catheter. The tubular portions of the valves 51, 52 can be tapered at one end, such that each valve 51, 52 forms a narrow slit 61, 62 at the distal end of each of the valves 51, 52. The slits 61, 62 can be positioned substantially at the center of each valve 51, 52. Slits 61, 62 comprise a pair of opposed lips that meet at two opposing corners. Slits 61, 62 are essentially closed to fluid inflow and nominally closed to fluid outflow. When fluid flows through the slits 61, 62, the lips separate and form an opening through which fluid can travel. When exposed to fluid flow in a first direction (represented by arrow) at a predetermined cracking pressure, the lips of the slits 61, 62 separate to form an opening. Cracking pressure is defined as the minimum fluid pressure necessary to open the slits 61, 62 of the valve members 51, 52 in a certain direction. The smaller the duckbill valve, generally the higher the pressure required to open the valve. Ideally, the valves 51, 52 will have a sufficiently low cracking pressure to allow fluid through when necessary. When exposed to fluid flow in a second direction (represented by arrows), the lips remain closed and prevent fluid from flowing through the duckbill valves 51, 52. Although shown as a straight slit 61, 62 in FIG. 14A, the slits can also be curved in shape. The width of slits 61, 62 can be adjusted, along with the angle, depth, or shape of the tapered design of the duckbill valves 51, 52, to fit the specific dimensions of the lumens 36, 39.

Valves 51, 52 are configured to provide a controlled antegrade (51) or retrograde (52) independent unidirectional fluid flow, respectively, within catheter lumens 36, 39. Typically, the antegrade flow, or flow of cleansed blood and dialysate fluid flowing into the lung cavity will be greater than the retrograde flow, or flow of dialysate flowing out of catheter lumen 39 and into the bladder. The valves 51, 52 can permit used dialysate to flow from the lung into the bladder, as will be described below, but can also prevent used dialysate fluid from re-entering or recirculating back into the lung.

Both valves 51, 52 remain closed if the static pressure in each of the lumens 36, 39 remains low enough, that is, where little or no pressure differential exists between the inside and outside of the valves 51, 52. If the static fluid pressure within the catheter lumen 36, 39 exceeds the static fluid pressure outside that portion of the catheter, then the valves 51, 52 can permit fluid flow. Thus, valve 51 opens only under positive pressure, or when the fluid in the catheter is pressurized to a level that is sufficiently above the pressure in the lung to force the valve 51 open for infusion of fluid such as dialysate fluid in the distal direction into the patient's lung. Valve 51 does not allow fluid to flow in the reverse direction back through lumen 36 toward the proximal end of the catheter, thereby preventing contaminated fluid from inadvertently refluxing back through the catheter. Valve 51 can remain closed despite the pressure of the displaced fluid against the one way valve 51. Application of a second vacuum at the proximal portion of the inflation lumen 63 can open the one way valve, releasing the displaced air or gas on the proximal end to the inflation/deflation device.

Aspiration valve 52 can be configured to permit fluid flow from outside to inside of the catheter lumen 39 of tube 5 for aspiration of fluid from the patient's lung. Valve 52 opens only under negative pressure, or when the fluid pressure in the catheter is lower than that of the lung by an amount sufficient to force the valve open for extraction of fluid from the patient's lung. Fluid flow into the lumen 39 is permitted when the fluid pressure outside valve 52 is higher than the pressure inside lumen 39 by an amount sufficient to force the slit 62 to open, thus permitting fluid aspiration from the patient's lung into the lumen 39. Valve 52 allows fluid to flow from the lung cavity through the distal tip 15 through aspiration lumen 39 into catheter tube 5 and the proximal end of the catheter to the bladder to be emptied, and prevents contaminated fluid from flowing back out of the proximal end of the catheter lumen 39 into the patient's body, as illustrated in FIG. 15.

Figure 15:
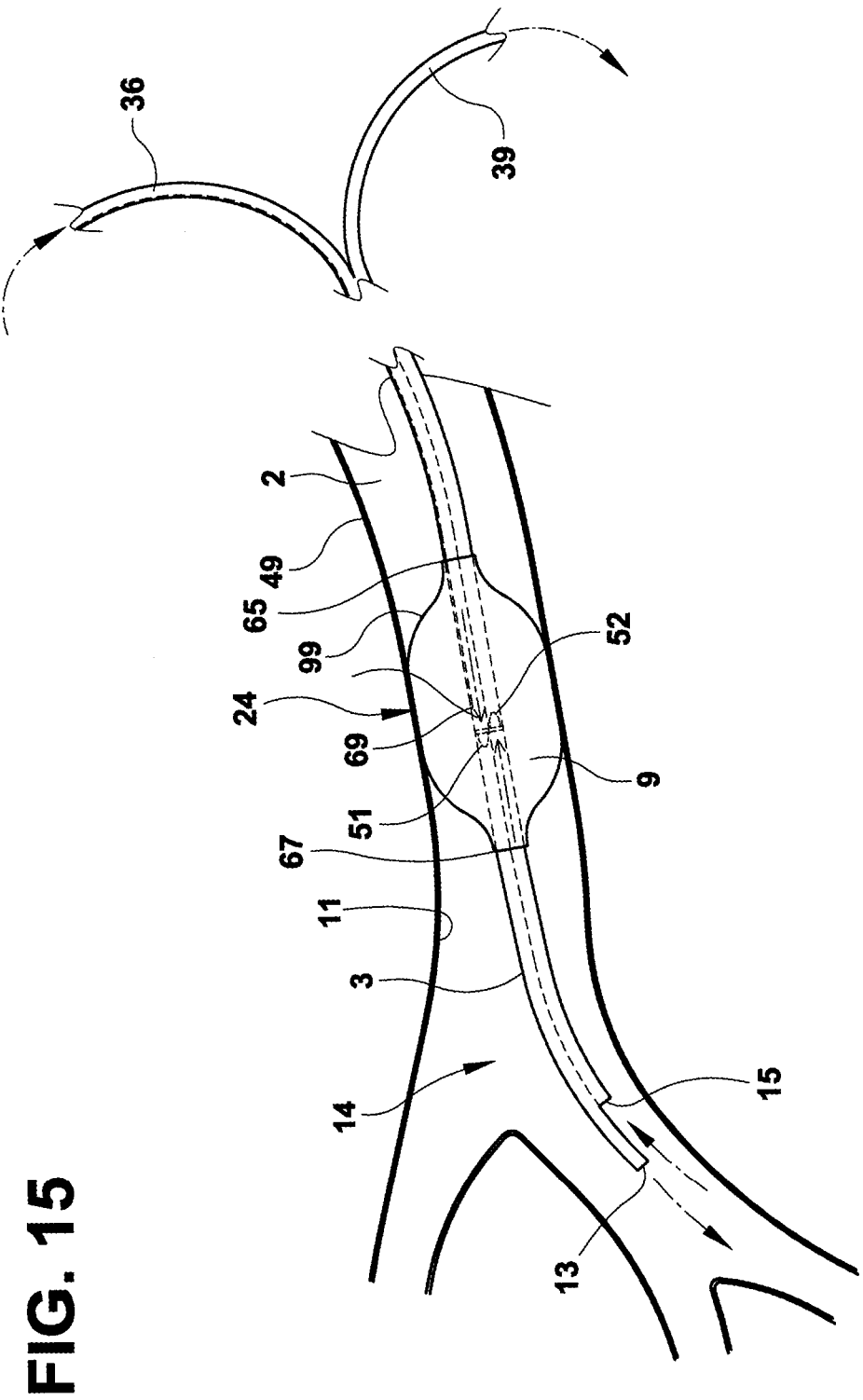
FIG. 15 illustrates a perspective view of the distal portion of the catheter of FIG. 13 inserted into a portion of a patient's bronchial vessel.
Figure 16:
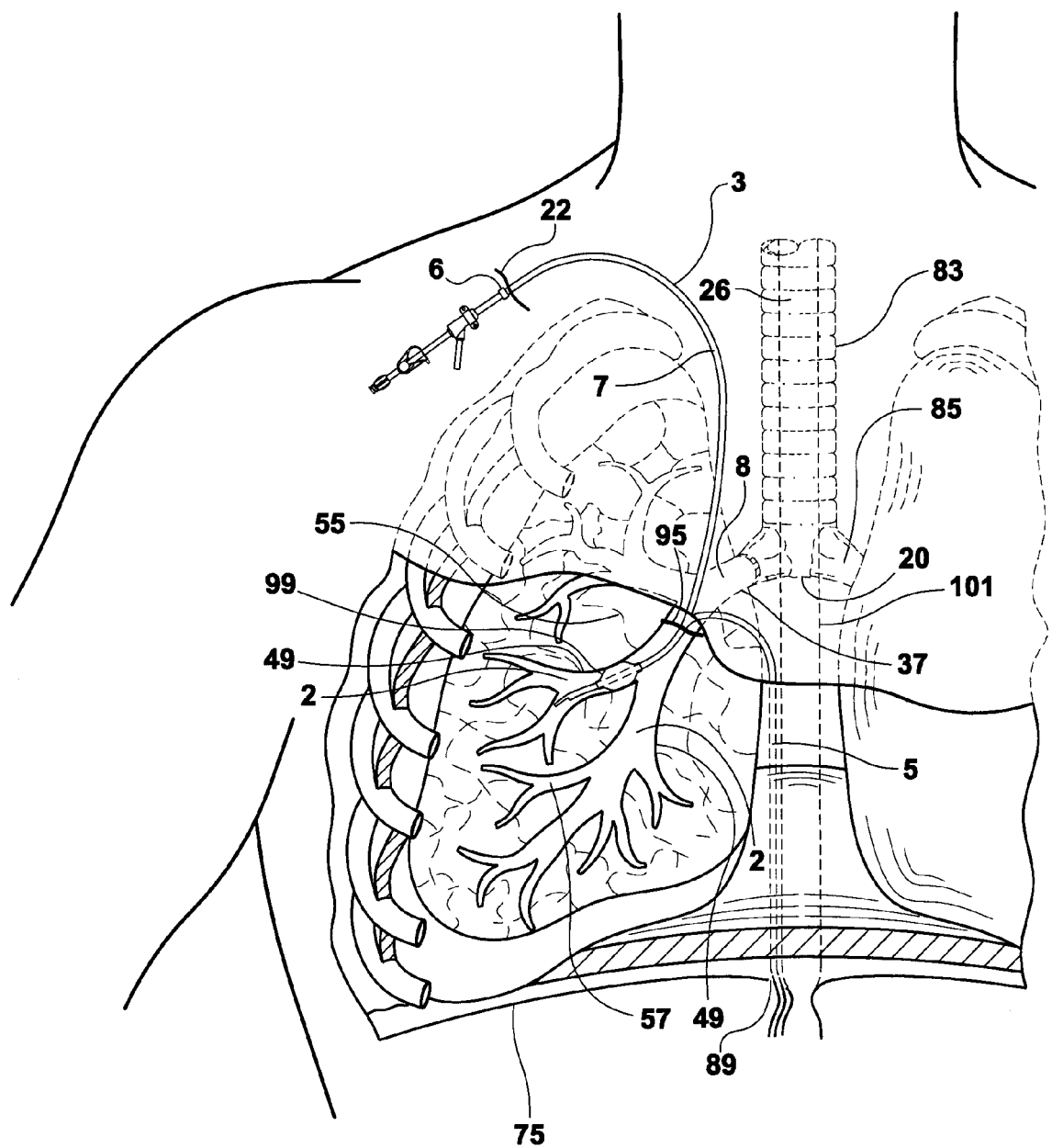
FIG. 16 illustrates a cutaway view of the distal portion of the catheter of FIG. 13 being inserted into a portion of the patient's bronchial vessel and a proximal portion of the catheter tubing being advanced toward a patient's diaphragm.
Figure 17:
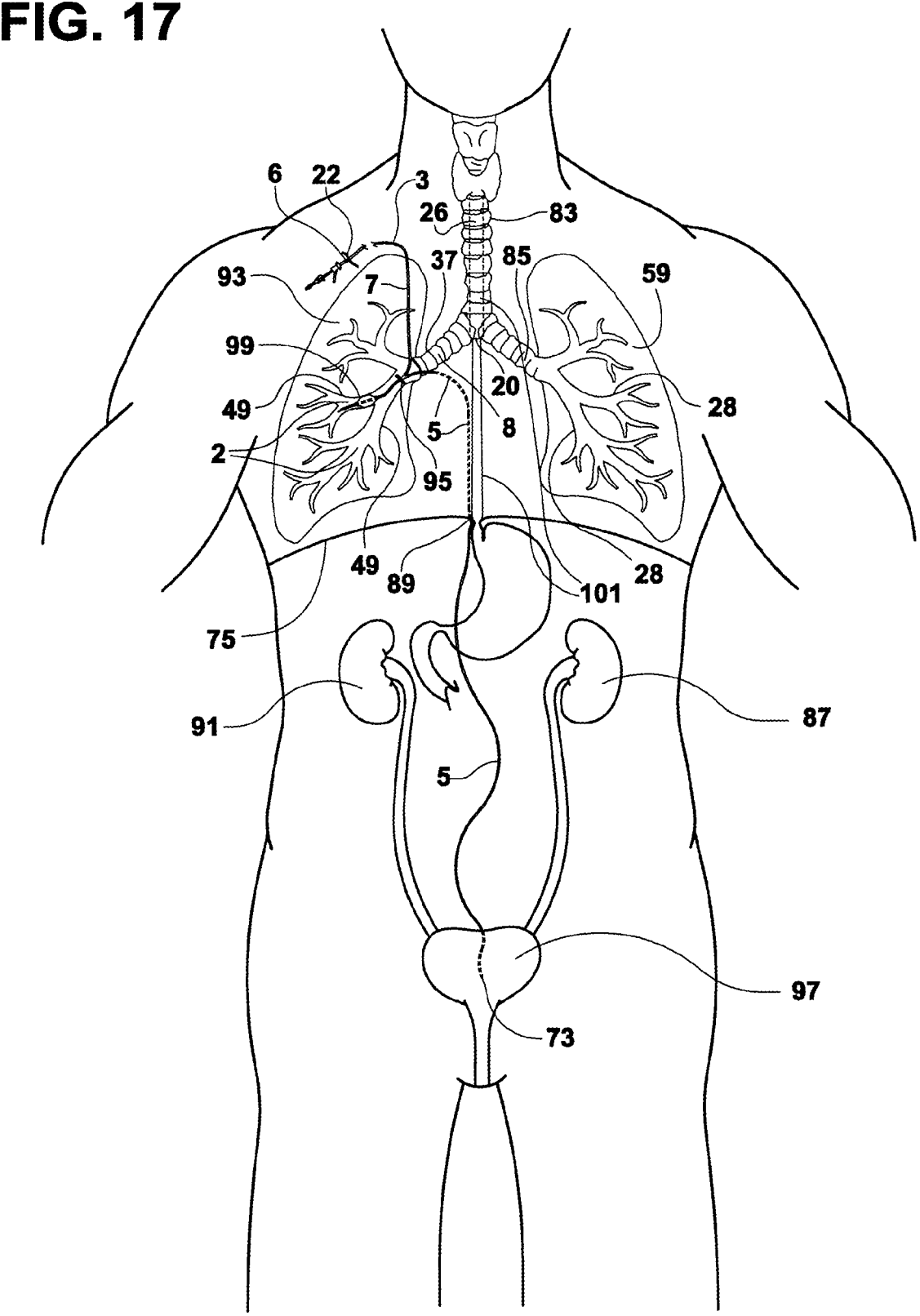
FIG. 17 illustrates an elevational schematic view of a distal portion of the catheter of FIG. 13 being inserted into a portion of a patient's bronchial vessel and a portion of the proximal portion of the catheter tubing being inserted into a patient's bladder.

Referring to FIGS. 15 through 17, a method of using the catheter assembly 1 illustrated in FIG. 13 is illustrated. In this method, the distal portion 14 of the catheter assembly 1 can be inserted into bronchi 49 of a human lung. At the point of insertion 95 of the catheter shaft 3 within the bronchi 49, the proximal end 34 of catheter tube 5 is tunneled through the parenchymal tissue 55 underneath the skin from the incision site 95 through the thoracic cavity to track alongside an outer wall of esophagus 101 into the abdominal cavity through a hole in the diaphragm called the esophageal hiatus 89. From there, tube 5 of the catheter shaft 3 extends through the abdominal cavity. An incision is made in a wall of a patient's bladder 97, and the proximal tip 73 of the catheter tube 5 is inserted into the bladder 97. Thus, in one aspect, contaminated fluid from dialysis treatments can be drained out of the lung into lumen 39 of catheter tube 5 into the patient's bladder 97 and disposed of through the urethra during a patient's normal excretory functions. Alternatively, the proximal end 34 of the catheter tube 5 can extend through the bladder 97 and out of the patient's urethra, where the distal tip 73 of the catheter can be securely connected to a drainage bag (not shown). This is advantageous for patients who may be supine or otherwise bedridden.

Dialysis can then be performed, as described above, except, in the method of using the valved catheter embodiment, one extension tube 19 of the catheter assembly 1 is connected to an infusion pump. Dialysate fluid can be infused into the lung through lumen 36. Contaminated dialysate can be expelled through the catheter tube 5 and into the bladder 97. The contaminated fluid flows by natural diffusion through catheter tube 5. After the fluid enters catheter tube 5, the flow of fluid out of the catheter assembly 1 through catheter tube 5 can be aided by the pull of gravity downward toward the bladder 97 after the fluid flows in a retrograde direction through the catheter lumen 39.

In summary, the method of using the valved catheter involves identifying a target lung region; determining the size of a bronchial vessel within the target lung region; providing a valved catheter having a sealing means, as described herein; deflating the means for sealing so as to allow it to be inserted into a bronchial vessel of the target lung region; inserting the catheter into the bronchial vessel; advancing the means for sealing to a position within a portion of the bronchial vessel; inflating the means for sealing until the means for sealing substantially occludes the bronchial vessel; infusing a dialysate solution into at least a portion of the target lung region through the infusion lumen at the distal end of the catheter; deflating the means for sealing; and removing the catheter from the target lung region.

Although primarily used for dialysis, the multilumen catheter described herein can also be used for other exemplary processes, such as, but not limited to, chemotherapy, and the delivery of medicaments such as therapeutic agents, including antibiotics or other medication, to the bodily organs, such as, but not limited to, lung parenchyma.

The method of use of any of the catheter assemblies described herein for dialysis treatment within a patient's lung is advantageous because in one aspect, the treatment chamber that is created by the expanded balloon 24 within a portion of the lungs isolates any possible infections from the rest of the body and allows bacteria to be physically contained within a finite treatment area, which allows for manageable treatment of infection. This presents a substantial advantage over both conventional hemodialysis and peritoneal dialysis, where infections can be quickly distributed throughout the entire body.

In another aspect, the method of using the lung to infuse dialysate solution is advantageous because the surface area to volume ratio of the lung is much more favorable than that of the peritoneum in peritoneal dialysis. Aside from the liver and kidneys, the lung has a high surface area per unit volume and a high level of vascularity. The lung has surfaces that are easily accessed via gases or fluids, and the lung has inner surfaces that can be contained and/or limited. The average pair of human lungs has a total lung capacity (TLC) about 5 to 6 liters of air, but only a small amount of this capacity is used during normal breathing. TLC includes inspiratory reserve volume, tidal volume, expiratory reserve volume, and residual volume. The total lung capacity depends on a patient's age, height, weight, and gender. The total surface area presented within this volume is approximately 70 $m^2$ in adults. In peritoneal dialysis, the surface area in contact with three liters of dialysate is estimated to be approximately 0.67 $m^2$. Calculations of surface area to volume indicate that the total lung volume required to present approximately 0.67 $m^2$ of surface area is approximately 57 mls, assuming a 70 $m^2$ surface area for a 6 liter lung. This equates to about 1.14% of the lung capacity of a 5 liter lung(s) or about 0.95% of the volume of a 6 liter lung(s). During normal breathing, the average person uses less than 10% of their total available lung capacity, and someone breathing heavily normally uses only 20% of their lung capacity. This implies that the use of approximately 1-2% of the lung as a filtration membrane for dialysis should not reduce other vital functions, such as, but not limited to, respiration and oxygen transport. Thus, the method described herein effectively eliminates issues associated with concentration gradients that form in the peritoneal cavity. This dramatically improves efficiency of the dialysis procedure.

Lung parenchymal dialysis is also advantageous because it can be performed regularly by a patient in a non-clinic setting. This allows patients to perform dialysis more frequently, compared to a clinic setting. More frequent dialysis reduces and/or eliminates many of the health issues associated with a standard clinic-based hemodialysis regimen. This includes a reduction in dietary constraints, elimination of long term pharmaceutical use, improved mortality rates, and a better overall quality of life for the patient.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". The words "including" and "having," as used herein including the claims, shall have the same meaning as the word "comprising." Those familiar with the art can recognize other equivalents to the specific embodiments described herein, which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions can be provided by alternative embodiments without departing from the scope of the appended claims. In this regard, for example, different combinations of elements and/or functions than those explicitly described above are also contemplated as can be set forth in some of the appended claims.

This completes the description of the selected embodiments of the invention. Those skilled in the art can recognize other equivalents to the specific embodiments described herein which equivalents are intended to be encompassed by the claims attached hereto.

What is claimed is:

1. A dialysis catheter assembly comprising:
   a catheter shaft having an elongated body extending along a longitudinal axis, a proximal portion and a distal portion, an outer catheter surface, and a first and second lumen extending therethrough, wherein the first lumen terminates in a first opening and the second lumen terminates in a second opening, wherein the first and second openings are disposed at the distal end of the catheter, and wherein the first opening is configured proximal of the second opening; and
   a means for sealing at least a portion of the lumen of the bronchial vessel, wherein the means for sealing comprises a flexible member coaxially disposed about a portion of the outer catheter surface proximal of the first and second openings, the flexible member having an inner flexible member surface and an outer flexible member surface, wherein the means for sealing is moveable between a collapsed insertion state and an expanded sealing state, and wherein the inner flexible member surface is in fluid communication with an inflation lumen.

2. The catheter assembly of claim 1, wherein the means for sealing comprises is a balloon.

3. The catheter assembly of claim 1, herein the means for sealing has a pre-formed expanded configuration.

4. The catheter assembly of claim 1, wherein when the means for sealing is in the expanded sealing state, at least a portion of the outer flexible member surface of the means for sealing engages the inner wall of the bronchial vessel lumen, thereby substantially sealing a portion of the bronchial vessel lumen.

5. The catheter assembly of claim 1, wherein in the expanded sealing state, the means for sealing has a maximum outer diameter, and wherein the maximum outer diameter is substantially equal to or greater than the inner diameter of the bronchial vessel lumen.

6. The catheter assembly of claim 1, wherein the means for sealing is capable of being inflated or deflated in response to infusion or withdrawal of at least one of: fluid, air, or gas through the inflation lumen.

7. The catheter assembly of claim 1, wherein the means for sealing further comprises at least one radially extending ridge, wherein the at least one ridge forms an integral part of the means for sealing, and wherein when the balloon is in the expanded state, the at least one ridge forms a substantially complete seal with the inner wall of the bronchial vessel.

8. The catheter assembly of claim 1, wherein the outer flexible member surface of the means for sealing is configured to conform to a space between at least two successive cartilaginous rings of at least one of: a trachea and a bronchial vessel, thereby forming a substantially complete seal.

9. The catheter assembly of claim 1, wherein the means for sealing further comprises a tubular mesh, and wherein at least a portion of the tubular mesh is operatively connected to at least a portion of the outer flexible member surface of the means for sealing.

10. The catheter of claim 1, wherein the means for sealing further comprises a self-expandable cage, wherein the cage comprises a plurality of radially extending ribs, and wherein at least a portion of the self-expandable cage is operatively connected to at least a portion of the inner flexible member surface of the means for sealing.

11. The catheter of claim 1, wherein the catheter comprises at least one valve, and wherein the valve is coupled to at least a portion of the at least one lumen of the catheter, and wherein the at least one valve is configured to open upon a pressure differential and permit fluid flow in one direction.

12. The catheter assembly of claim 1, wherein the catheter further comprises at least one collar, wherein the at least one collar is operatively coupled to the outer surface of the catheter shaft, and wherein the at least one collar is configured to secure at least a portion of the catheter shaft within a portion of the bronchial vessel.

13. A method of using a dialysis catheter, wherein the method comprises:
   providing a catheter comprising:
      a catheter shaft having an elongated body extending along a longitudinal axis, a proximal portion and a distal portion, an outer catheter surface, and a first and second lumen extending therethrough, wherein the first lumen terminates in a first opening and the second lumen terminates second opening, wherein the first and second openings are disposed at the distal end of the catheter, and wherein the first opening is configured proximal of the second opening; and
      a means for sealing at least a portion of the lumen of the bronchial vessel, wherein the means for sealing comprises a flexible member coaxially disposed about a portion of the outer catheter surface proximal of the first and second openings, the flexible member having an inner flexible member surface and an outer flexible member surface, wherein the means for sealing is moveable between a collapsed insertion state and an expanded sealing state, and wherein the inner flexible member surface is in fluid communication with an inflation lumen;
   identifying a target lung region, wherein the target lung region comprises at least one bronchial vessel;
   inserting at least a portion of the distal portion of the catheter shaft into a portion of the target lung region;
   inflating the at least one means for sealing to form a substantially complete seal between a portion of the outer surface of the means for sealing and a portion of the inner wall of the bronchial vessel;
   infusing a dialysate solution into a portion of the target lung region.

14. The method of claim 13, wherein the method further comprises deflating the means for sealing before inserting at least a portion of the distal portion of the catheter shaft into at least a portion of the bronchial vessel lumen such that the means for sealing is in a collapsed insertion state.

15. The method of claim 13, wherein the method further comprises determining the diameter of the bronchial lumen before inserting at least a portion of the distal portion of the catheter shaft into at least a portion of the bronchial vessel lumen.

16. The method of claim 13, wherein the method further comprises advancing at least a portion of the distal portion of the catheter assembly into a portion of a patient's trachea further into a patient's bronchi after inserting the catheter assembly.

17. The method of claim 13, wherein the method further comprises advancing at least a portion of the distal portion of the catheter assembly into a portion of the bronchial vessel through the outer wall of the bronchial vessel after inserting the catheter assembly.

18. The method of claim 13, wherein the method further comprises identifying at least one intercostal space before inserting the distal portion of the catheter assembly, and advancing the catheter assembly into the intercostal space.

19. The method of claim 13, wherein the method further comprises advancing the distal portion of the catheter into a portion of a bronchial vessel after inserting the distal portion of the catheter assembly into a target lung region.

20. The method of claim 13, wherein the method further comprises introducing one of at least air, a fluid, or a gas into the sealing means after the catheter assembly is inserted, such that when the sealing means is radially expanded, a portion of the outer flexible member surface of the means for sealing engages a portion of the inner wall of the bronchial vessel sufficiently to form a substantially complete seal of the bronchial lumen.

21. The method of claim 20, wherein the method further comprises infusing a fluid into the catheter assembly and into the bronchial vessel, wherein the fluid is selected from the group comprising: a dialysate fluid, a medicament, and a contrast agent.

22. The method of claim 13, wherein the method further comprises withdrawing contaminated fluid from the target lung region for drainage.

23. The method of claim 13, wherein the method further comprises:
   withdrawing a bodily fluid to be treated from the bronchial vessel;
   treating the bodily fluid; and
   infusing the treated fluid into the bronchial vessel through the catheter assembly.

24. The method of claim 20, wherein the method further comprises infusing a dialysate solution through the catheter assembly and into the target lung region, wherein the dialysate solution comprises a therapeutically effective amount of at least one of: sodium, potassium, chloride, calcium, magnesium, bicarbonate, acetate, water, and dextrose.

25. The method of claim 13, wherein the method further comprises inserting at least a portion of the proximal portion of the catheter assembly into a patient's bladder, thereby allowing contaminated fluid to empty through the patient's bladder and urethra.

26. The method of claim 13, wherein the method further comprises selectively deflating the means for sealing and removing the catheter the target lung region.

27. A method for dialysis treatment of a patient using an indwelling catheter device, wherein the method comprises;
   providing an indwelling catheter assembly comprising:
      a catheter shaft having an elongated body extending along a longitudinal axis, a proximal portion and a distal portion, an outer catheter surface, a first and second lumen extending therethrough, wherein the first lumen terminates in a first opening and the second lumen terminates in a second opening, wherein the first and second openings are disposed at the distal end of the catheter, and wherein the first opening is configured proximal of the second opening; and
      a means for sealing at least a portion of a bronchial vessel of a patient, wherein the means for sealing comprises a flexible member coaxially disposed about a portion of the outer catheter surface proximal of the first and second openings, the flexible member having an inner flexible member surface and an outer flexible member surface, wherein the means for sealing is moveable between a collapsed insertion state and an expanded sealing state, and wherein the inner flexible member surface is in fluid communication with an inflation lumen;
   inserting the distal portion of the catheter into the bronchial vessel; and
   sealing at least a portion of the bronchial vessel by expanding the means for sealing.

* * * * *